(12) United States Patent
Behlke et al.

(10) Patent No.: US 9,081,737 B2
(45) Date of Patent: Jul. 14, 2015

(54) METHODS FOR PREDICTING STABILITY AND MELTING TEMPERATURES OF NUCLEIC ACID DUPLEXES

(75) Inventors: Mark Behlke, Coralville, IA (US); Richard Owczarzy, Coralville, IA (US); Scott D. Rose, Coralville, IA (US); Andrey Tataurov, Iowa City, IA (US); Yong You, Iowa City, IA (US)

(73) Assignee: Integrated DNA Technologies, Inc., Coralville, IA (US)

(*) Notice: Subject to any disclaimer, the term of this patent is extended or adjusted under 35 U.S.C. 154(b) by 369 days.

(21) Appl. No.: 13/194,790

(22) Filed: Jul. 29, 2011

(65) Prior Publication Data

US 2012/0029891 A1 Feb. 2, 2012

Related U.S. Application Data

(60) Provisional application No. 61/370,040, filed on Aug. 2, 2010.

(51) Int. Cl.
| | |
|---|---|
| G06F 7/60 | (2006.01) |
| G06F 17/10 | (2006.01) |
| G06F 19/16 | (2011.01) |
| G01K 11/06 | (2006.01) |
| C12Q 1/68 | (2006.01) |
| G06F 19/18 | (2011.01) |
| G06F 19/20 | (2011.01) |

(52) U.S. Cl.
CPC .............. *G06F 19/16* (2013.01); *C12Q 1/6816* (2013.01); *G01K 11/06* (2013.01); *G06F 19/18* (2013.01); *G06F 19/20* (2013.01)

(58) Field of Classification Search
CPC ..................................................... G01K 11/06
See application file for complete search history.

(56) References Cited

U.S. PATENT DOCUMENTS

| | | | |
|---|---|---|---|
| 6,268,490 | B1 | 7/2001 | Imanishi et al. |
| 6,734,291 | B2 | 5/2004 | Kochkine et al. |
| 6,794,499 | B2 | 9/2004 | Wengel et al. |
| 6,889,143 | B2 | 5/2005 | Behlke et al. |
| 7,569,686 | B1 | 8/2009 | Bhat et al. |
| 7,741,457 | B2 | 6/2010 | Seth et al. |
| 2003/0235822 | A1 | 12/2003 | Lokhov et al. |
| 2004/0219565 | A1* | 11/2004 | Kauppinen et al. ............... 435/6 |

FOREIGN PATENT DOCUMENTS

EP 1 882 748 A2 1/2008

OTHER PUBLICATIONS

McTigue et al. "Sequence-Dependent Thermodynamic Parameters for Locked Nucleic Acid (LNA)-DNA Duplex Formation", Biochemistry, vol. 43, No. 18, 2004.*

International Search Report from International Application No. PCT/US2011/046010, mailed Dec. 6, 2011.

(Continued)

*Primary Examiner* — Saif Alhija
(74) *Attorney, Agent, or Firm* — McDonnell Boehnen Hulbert & Berghoff LLP.

(57) ABSTRACT

The present invention provides methods that more accurately predict melting temperatures for duplex oligomers. The invented methods predict the $T_m$ of chimeric duplexes containing various amounts of locked nucleic acid modifications in oligonucleotide strands.

10 Claims, 6 Drawing Sheets

(56) References Cited

OTHER PUBLICATIONS

Borer et al., "Stability of ribonucleic acid double-stranded helices," J Mol Biol. 86(4):843-53 (1974).
Fasman ed., "Handbook of Biochemistry and Molecular Biology, Nucleic Acids Volume I" pp. 589 (CRC Press 3rd Ed. 1975).
Gray, "Derivation of Nearest-Neighbor Properties from Data on Nucleic Acid Oligomers. I. Simple Sets of Independent Sequences and the Influence of Absent Nearest Neighbors," Biopolymers 42(7):783-93 (1997).
Gray, "Derivation of Nearest-Neighbor Properties from Data on Nucleic Acid Oligomers. II. Thermodynamic Parameters of DNA-RNA Hybrids and DNA Duplexes," Biopolymers 42(7):795-810 (1997).
Henegariu et al., "Multiplex PCR: critical parameters and step-by-step protocol," Biotechniques 23(3):504-11 (1997).
Hughesman et al., "Role of the Heat Capacity Change in Understanding and Modeling Melting Thermodynamics of Complementary Duplexes Containing Standard and Nucleobase-Modified LNA," Biochemistry 50(23):5354-68 (2011).
Jacobsen et al., "LNA-enhanced detection of single nucleotide polymorphisms in the apolipoprotein E," Nucleic Acids Res. 30(19):e100 (2002).
Jensen et al., "A comparison of the solution structures of an LNA:DNA duplex and the unmodified DNA:DNA duplex," J Chem Soc 2(7):1224-32 (2001).
Kierzek et al., "The influence of locked nucleic acid residues on the thermodynamic properties of 20-O-methyl RNA/RNA heteroduplexes," Nucleic Acids Research 33(16):5082-93 (2005).
Kleppe et al., "Studies on polynucleotides. XCVI. Repair replications of short synthetic DNA's as catalyzed by DNA polymerases," J Mol Biol. 56(2):341-61 (1971).
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," Tetrahedron 54(14):3607-30 (1998).
Kutyavin et al., "3'-minor groove binder-DNA probes increase sequence specificity at PCR extension temperatures," Nucleic Acids Res. 28(2):655-61 (2000).
Markoulatos et al., "Multiplex polymerase chain reaction: a practical approach," J Clin Lab Anal. 16(1):47-51 (2002).
Marky & Breslauer, "Calculating Thermodynamic Data for Transitions of any Molecularity from Equilibrium Melting Curves," Biopolymers 26(9):1601-20 (1987).
McTigue et al., "Sequence-dependent thermodynamic parameters for locked nucleic acid (LNA)-DNA duplex formation," Biochemistry 43(18) 5388-405 (2004).
Moreira et al., "Effects of Fluorescent Dyes, Quenchers and Dangling Ends on DNA Duplex Stability," Biochem Biophys Res Commun 327(2):473-84 (2005).
Nielsen et al., "Solution Structure of an LNA Hybridized to DNA: NMR Study of the d(CTLGCTLTLCTLGC):d (GCAGAAGCAG) Duplex Containing Four Locked Nucleotides," Bioconjugate Chem 11(2):228-38 (2000).
Ørum et al., "Detection of the factor V Leiden mutation by direct allele-specific hybridization of PCR amplicons to photoimmobilized locked nucleic acids," Clin Chem. 45(11):1898-905 (1999).
Ørum & Wengel, "Locked nucleic acids: a promising molecular family for gene-function analysis and antisense drug development," Curr Opin Mol Ther. 3(3):239-43 (2001).
Owczarzy et al., "Predicting stability of DNA duplexes in solutions containing magnesium and monovalent cations," Biochemistry 47(19):5336-53 (2008).
Owczarzy et al., "Effects of Sodium Ions on DNA Duplex Oligomers: Improved Predictions of Melting Temperatures," Biochemistry 43(12)3537-54 (2004).
Owczarzy et al., "IDT SciTools: a suite for analysis and design of nucleic acid oligomers," Nucleic Acids Research 36(Supp2) W163-69 (2004).
Owczarzy et al., "Predicting Sequence-Dependent Melting Stability of Short Duplex DNA Oligomers," Biopolymers 44(3):217-39 (1997).
Petersen & Wengel, "LNA: a versatile tool for therapeutics and genomics," TRENDS in Biotechnology 21(2):74-81 (2003).
Saiki et al., "Enzymatic amplification of beta-globin genomic sequences and restriction site analysis for diagnosis of sickle cell anemia," Science 230(4732):1350-54 (1985).
Santa Lucia, "A unified view of polymer, dumbbell, and oligonucleotide DNA nearest-neighbor thermodynamics," Proc Nat'l Acad Sci 95(4):1460-65 (1998).
Santa Lucia & Hicks, "The thermodynamics of DNA structural motifs," Annu Rev Biophys Biomol Struct 33:415-40 (2004).
Sørensen et al., "α-L-ribo-Configured Locked Nucleic Acid (α-L-LNA): Synthesis and Properties," J Am Chem Soc. 124(10):2164-76 (2002).
Tolstrup et al., "OligoDesign: optimal design of LNA (locked nucleic acid) oligonucleotide capture probes for gene expression profiling," Nucleic Acids Research 31(13):3758-62 (2003).
Wetmur, "DNA probes: applications of the principles of nucleic acid hybridization," Critical Reviews in Biochemistry and Molecular Biology 26(3-4):227-59 (1991).
You et al., "Measuring Thermodynamic Details of DNA Hybridization Using Fluorescence," Biopolymers 95(7):472-86 (2010).
You et al., "Design of LNA probes that improve mismatch discrimination," Nucleic Acids Research 34(8):e60 1-11 (2006).
International Preliminary Report on Patentability from International Application No. PCT/US2011/046010, issued Feb. 5, 2013, pp. 1-8.

* cited by examiner

Figure 1

```
LOCUS       NM_008493              3257 bp    mRNA    linear   ROD 21-MAR-
2010
DEFINITION  Mus musculus leptin (Lep), mRNA.

LOCUS       NT_039340           27702811 bp    DNA     linear   CON 20-JUN-
2007
DEFINITION  Mus musculus chromosome 6 genomic contig, strain C57BL/6J.
ACCESSION   NT_039340 NT_078517 NT_094688
VERSION     NT_039340.7  GI:149254897
KEYWORDS    .
SOURCE      Mus musculus (house mouse)
```

GCTCCGTGGCTCCCAGTCAGTCGATGACAGGAAGTAAGGGCCTGGACCAGGAAGGTGAGAAGGGAGGGAGGTAGCCCA
CGTTCACAGATGTAATGAAGGGCTCTGGAGACCGATCTCCCTGGTCACTTGCTAAAGCACCTCTTGTTCTCTTCCTC
CTGCATAGCAGTCGGTATCCGCCAAGCAGAGGGTCATGGCTTGGACTTCATCCTGGGCTTCACCCCATTCTGAGT
TTGTCCAAGATGGACCAGACTCTGGCAGTCTATCAACAGGTCCTCACCAGC<u>TGCTTCC</u>AAAATGTGCTGCAGAT
AGCCAATGACCTGGA<u>AAATCTCC</u>(C/T)<u>GAGACCTCC</u>TCCATCTGCTGG<u>CCTTCTCCAAGAGCTGCTCC</u>TTGCCTCAG
ACCAGTGGCTGCAAGGCCAGAGACCTGGATGGCGTTCTGGGAAGCCTCACTCTACTGACGAGGTGTGTGCTTT
GAGCAGCCTGCAGGGCTCTCTGCACGACATTCTTCAACAGTTGGATGTTAGCCCTGAATCTGAAGTTTCAAAGCCC
ACTGGGCTCCAAGAATCATGTAGAGGGAAGAAACCTTGCTTCCAGGGGTCTTCAGGAGAAGCGAGCCATGTGCAC
ACATCCATCATTCATTTGCCTCCGTCCTGTAGACCACCCATCCAAAGGCATGACTCCACAATGCTTGACTCAAGTTA
TCCACACAACTTCATGAGCACAAGGAGGGC

Mm Lep C/T SNP
                                       M          MM
Mm Lep ObC SNP HEX
AGAATCT*C*C*GAGACCT                66.7        54.9
Mm Lep ObT SNP FAM
AGAATCT*C*T*GAGACCTC                62.7        57.8

Mm Lep For1
CAGTCTATCAACAGGTCCTCAC

Mm Lep Rev2
GAGCAGCTCTTGGAGAAGG
(CTTCTCCAAGAGCTGCTCC)

METHODS FOR PREDICTING STABILITY AND MELTING TEMPERATURES OF NUCLEIC ACID DUPLEXES

CROSS REFERENCE TO RELATED APPLICATION

This application claims the benefit of priority from U.S. Provisional Application No. 61/370,040, filed Aug. 2, 2010, the disclosure of which is incorporated by reference herein in its entirety.

FIELD OF THE INVENTION

This invention pertains to new thermodynamic parameters that provide accurate predictions of stability and melting temperature for oligonucleotides containing multiple LNA modifications. Specifically, the invention provides parameters for both perfectly matched base pairs and single base mismatches.

BACKGROUND OF THE INVENTION

Hybridization between complementary nucleic acids is an implicit feature in the Watson-Crick model for DNA structure that is exploited for many applications of the biological and biomedical arts. For example, virtually all methods for replicating and/or amplifying nucleic acid molecules are initiated by a step in which a complementary oligonucleotide (typically referred to as a "primer") hybridizes to some portion of a "target" nucleic acid molecule. A polymerase then synthesizes a complementary nucleic acid from the primer, using the target nucleic acid as a "template." See Kleppe et al., 1971 *J. Mol. Biol.* 56: 341-61.

One particular application, known as the polymerase chain reaction, PCR, is widely used in a variety of biological and medical arts. For a description, see Saiki et al., 1985, *Science* 230: 1350-54. In PCR, two or more primers are used that hybridize to separate regions of a target nucleic acid and its complementary sequence. The sample is then subjected to multiple cycles of heating and cooling, repeatedly hybridizing and dissociating the complementary strands so that multiple replications of the target nucleic acid and its complement are performed. As a result, even very small initial quantities of a target nucleic acid may be enormously increased, or "amplified," for subsequent uses (e.g., for detection, sequencing, etc.).

Multiplex PCR is a particular version of PCR in which several different primers are used to amplify and detect a plurality of different nucleic acids in a sample—usually ten to a hundred or more different target nucleic acids. Thus, the technique allows a user to amplify and evaluate large numbers of different nucleic acids simultaneously in a single sample. The enormous benefits of high throughput, speed and efficiency offered by this technique has made multiplex PCR increasingly popular. However, achievement of successful multiplex PCR usually involves empirical testing as existing computer programs that pick and/or design PCR primers have errors. In multiplex PCR, the errors become additive and therefore good results are seldom achieved without some amount of trial and error. See Markouatos et al., 2002, *J. Clin. Lab Anal.* 16(1): 47-51; Henegarin et al., 1997, *Biotechniques* 23(3): 504-11.

Some applications using probes and primers are designed to distinguish between two or more sequences that differ by one or more nucleotides, such as assays designed for single nucleotide polymorphism (SNP) detection. In these assays, mutations of clinical significance differ by a single nucleotide from the wild-type sequence.

Stability and melting temperature, $T_m$, of nucleic acid duplexes is a key design parameter for a variety of applications utilizing DNA and RNA oligonucleotides (Petersen and Wengel, 2003, *Trends Biotechnol.* 21: 74-81; You et al., 2006, *Nucleic Acids Res.*, 34: e60). The successful implementation of all techniques involving nucleic acid hybridization (including the exemplary techniques described, supra) is dependent upon the use of nucleic acid probes and primers that specifically hybridize with complementary nucleic acids of interest while, at the same time, avoiding non-specific hybridization with other nucleic acid molecules that may be present. For a review, see Wetmur, 1991, *Critical Reviews in Biochemistry and Molecular Biology* 26: 227-59. These properties are even more critical in techniques, such as multiplex PCR and microarray hybridization, where a plurality of different probes or primers is used, each of which may be specific for a different target nucleic acid.

Various modifications are available that can significantly affect the $T_m$ of a nucleic acid duplex. The modifications can be placed at a terminal end, such as a minor groove binder (MGB) (Kutyavin et al., 2000, *Nucleic Acids Research*, 28(2): 655-61). The modifications can be placed on the backbone of the oligonucleotide, examples of which include phosphorothioates, phosphorodithioates and phosphonoacetates. The modifications can be located on the sugar moiety, examples of which include locked nucleic acids (LNAs), 2'-O-methyls, 2'-methoxyethylriboses (MOE's), ENA's (ethylene bicyclic nucleic acids). The modification can be located on the base moiety, examples of which include 5-methyl-dC and propynyl-dU and propynyl-dC.

LNAs are RNA modifications wherein a methyl bridge connects the 2'-oxygen and the 4'-carbon, locking the ribose in an A-form conformation, providing synthetic oligonucleotides with unique properties (Koshkin et al., 1998, *Tetrahedron* 54: 3607-30; U.S. Pat. No. 6,268,490). LNA modifications increase the stability of nucleic acid duplexes and the specificity of oligonucleotide binding to complementary sequences, e.g., genomic DNAs (Petersen and Wengel, 2003). Therefore, oligonucleotides containing LNA modifications may be used to improve accuracy and sensitivity of various biological applications and assays, e.g., antisense oligonucleotides, nucleic acid microarrays, sequencing, PCR primers, PCR probes and medical diagnostics.

Preliminary work has been performed to develop thermodynamic parameters for DNA duplexes containing an LNA modification (see McTigue et al., 2004, *Biochemistry* 43(18): 5388-05). McTigue et al. improved upon the older model of $T_m$ prediction simply based upon the number of LNA additions and described sequence-dependent thermodynamic parameters for duplex formations containing a single LNA modification.

Since duplexes containing a single LNA analog represent only a fraction of LNA-containing duplexes, there is a need for sequence-dependent thermodynamic parameters for duplexes containing multiple LNA analogs, especially those containing multiple adjacent LNA analogs. The present invention includes methods to predict the stability and $T_m$ of chimeric duplexes containing various amounts of locked nucleic acid modifications in oligonucleotide strands. These and other advantages of the invention, as well as additional inventive features, will be apparent from the description of the invention provided herein.

BRIEF SUMMARY OF THE INVENTION

The invention provides methods that more accurately predict melting temperatures for duplex oligomers than current methods. The disclosed methods predict the $T_m$ of chimeric duplexes containing various amounts of locked nucleic acid modifications in oligonucleotide strands. The method of the invention can be incorporated within a wide variety of software applications that utilize calculation of melting temperature of LNA:DNA duplex oligomers. The method can be employed in any software for use in calculating melting temperature of DNA duplex oligomers containing multiple or, in a further embodiment, consecutive LNA modifications or mismatched LNA base pairs. In one embodiment, the methods can be incorporated into design programs for polymerase chain reaction, 5'nuclease assays, nucleic acid secondary structure prediction, and programs that calculate physicochemical properties of DNA oligomers.

In one embodiment, the present invention provides a method of predicting the melting temperature of an oligonucleotide comprising:

(a) a computer system receiving a data input from a user, the computer comprising a processor, and instructions executable by the processor;

(b) responsive to the data input from a user, the computer system calculating a $T_m$ value using the equation:

$$T_m = \frac{\Delta H^o}{\Delta S^o + R\ln(C_1 - C_2/2)}; \text{ and}$$

wherein $\Delta H^o = \Delta H^o_{DNA} + \Delta\Delta H^o_{LNA}$, $\Delta S^o = \Delta S^o_{DNA} + \Delta\Delta S^o_{LNA}$, $$\Delta\Delta H^o_{LNA} = \sum_{i,j=A,C,G,T} N^{n-n}_{ij} \Delta\Delta H^{n-n}_{ij}, \Delta\Delta S^o_{LNA} = \sum_{i,j=A,C,G,T} N^{n-n}_{ij} \Delta\Delta S^{n-n}_{ij}$$

(c) providing an output to a display,
wherein the oligonucleotide comprises at least two Locked Nucleic Acid (LNA) modifications.

In another embodiment, the present invention provides a method of predicting the melting temperature of an oligonucleotide comprising:

(a) a networked server receiving data input from a communication device associated with a user, the server comprising the communication interface, a processor, and instructions executable by the processor;

(b) responsive to receiving the data input, the networked server sending via the communication interface to the communication device, calculation of a $T_m$ value using the equation:

$$T_m = \frac{\Delta H^o}{\Delta S^o + R\ln(C_1 - C_2/2)}; \text{ and}$$

wherein $\Delta H^o = \Delta H^o_{DNA} + \Delta\Delta H^o_{LNA}$, $\Delta S^o = \Delta S^o_{DNA} + \Delta\Delta S^o_{LNA}$, $$\Delta\Delta H^o_{LNA} = \sum_{i,j=A,C,G,T} N^{n-n}_{ij} \Delta\Delta H^{n-n}_{ij}, \Delta S^o_{LNA} = \sum_{i,j=A,C,G,T} N^{n-n}_{ij} \Delta\Delta S^{n-n}_{ij}$$

(c) sending the $T_m$ value via the communication interface to the user communication device,
wherein the oligonucleotide comprises at least two Locked Nucleic Acid (LNA) modifications.

In an additional embodiment, the user interacts with the networked server via a web-browsing application running on the communication device.

In a further embodiment, the communication device comprises at least one of a computer, a desktop computer, or a laptop computer.

In additional embodiments, all values of $\Delta\Delta H^o_{LNA}$ and $\Delta\Delta S^o_{LNA}$ are determined using nearest neighbor parameters.

In one embodiment, the present invention provides a method of predicting the stability of an oligonucleotide comprising:

(a) a computer system receiving a data input from a user, the computer comprising a processor, and instructions executable by the processor;

(b) responsive to the data input from a user, the computer system calculating a free energy value using the equation:

$$\Delta G^o = \Delta G^o_{DNA} + \Delta\Delta G^o_{LNA}; \text{ and } \Delta\Delta G^o_{LNA} = \sum_{i,j=A,C,G,T} N^{n-n}_{ij} \Delta\Delta G^{n-n}_{ij}$$

(c) providing an output to a display,
wherein the oligonucleotide comprises at least two Locked Nucleic Acid (LNA) modifications.

In an additional embodiment, the present invention provides a method of predicting the stability of an oligonucleotide comprising:

(a) a networked server receiving data input from a communication device associated with a user, the server comprising the communication interface, a processor, and instructions executable by the processor;

(b) responsive to receiving the data input, the networked server sending via the communication interface to the communication device, calculation of a free energy value using the equation:

$$\Delta G^o = \Delta G^o_{DNA} + \Delta\Delta G^o_{LNA}; \text{ and } \Delta\Delta G^o_{LNA} = \sum_{i,j=A,C,G,T} N^{n-n}_{ij} \Delta\Delta G^{n-n}_{ij}$$

(c) sending the free energy value via the communication interface to the user communication device,
wherein the oligonucleotide comprises at least two Locked Nucleic Acid (LNA) modifications.

In a further embodiment, the user interacts with the networked server via a web-browsing application running on the communication device.

In additional embodiments, the communication device comprises at least one of a computer, a desktop computer, or a laptop computer.

In additional embodiments, all values of $\Delta\Delta G^o_{LNA}$ are determined using nearest neighbor parameters.

BRIEF DESCRIPTION OF THE DRAWINGS

FIG. 1 shows the sequence of mouse Leptin to be used for a LNA probe-based genotyping assay. The single nucleotide polymorphism (SNP) is denoted within the sequence. Probe and primer sequences, as well as Tm for matched (M) and mismatched (MM) probes are presented.

DETAILED DESCRIPTION OF THE INVENTION

Figure 2:
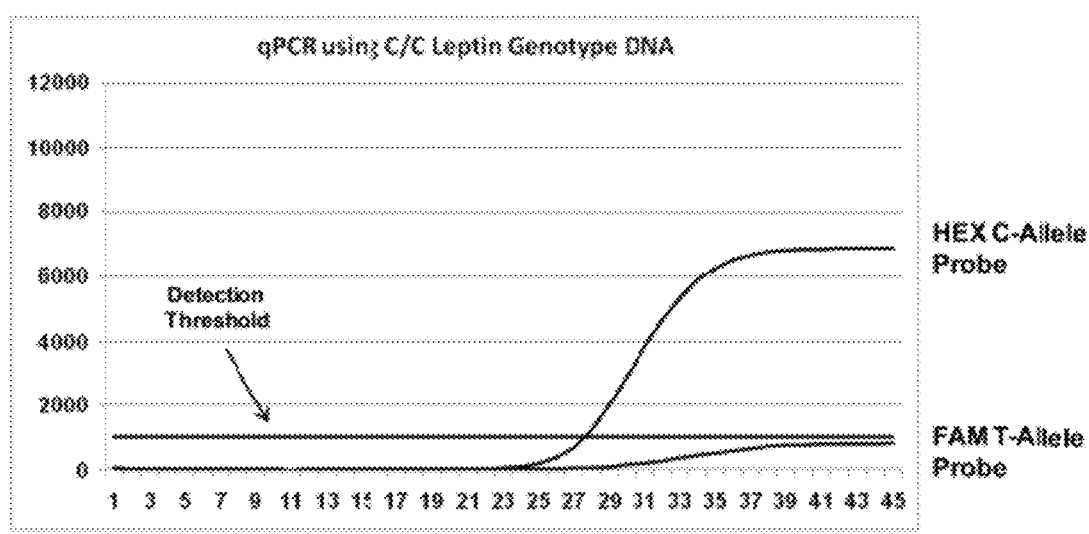
FIG. 2 shows an amplification plot of a real-time PCR reaction performed using genomic DNA homozygous for the C leptin locus (C/C genotype). Cycle number is shown on the X-axis and relative fluorescence is shown on the Y-axis. The HEX labeled C-specific probe showed positive signal whereas the FAM labeled T-specific probe remained undetectable at background levels.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The present invention provides a method that more accurately predicts stability and melting temperatures for duplex oligomers than methods in routine use today. The new methods predict stability and Tm of chimeric duplexes containing various amounts of locked nucleic acid modifications in oligonucleotide strands. The new methods are compatible with the nearest neighbor thermodynamic model of RNA and DNA duplexes (Borer et. al, 1974, *J. Mol. Biol.* 86: 843-53; Santa Lucia, 1998, *Proc. Natl. Acad. Sci. U.S.A.*, 95: 1460-65; Owczarzy et al., 1997, *Biochemistry* 43: 3537-54), providing accurate melting temperature predictions for duplexes containing consecutive LNA-DNA base pairs. The melting temperature of a nucleic acid oligomeric duplex is ordinarily estimated using the following formula, $$T_m = \frac{\Delta H^\circ}{\Delta S^\circ R \ln(C_1 - C_2/2)} \tag{1}$$

where R is the ideal gas constant (1.9865 cal/(mol·K)). The $C_1$ and $C_2$ are concentrations of nucleic acid single strands that anneal to form a duplex. It is assumed in equation (1) that $C_1 \geq C_2$. A person skilled in biophysics will recognize that melting temperature predicted by equation (1) will be in units of Kelvin and can easily be converted to other units of temperature using conversion formulas known in the art. For example, melting temperatures in degrees of Celsius (° C.) are readily obtained from melting temperatures in Kelvins by the following relationship, $T_m(°C.)=T_m(K)-273.15$.

Stability of a nucleic acid oligomeric duplex in the form of free energy values is ordinarily estimated using the following formula, $$\Delta G^\circ = \Delta H^\circ - T\Delta S^\circ$$

where $\Delta G^\circ$ values are generally determined at 37° C. (Santa Lucia, 1998).

Nearest-neighbor model provides predictions of sequence-dependent nucleic acid stability (Borer et al., 1974; Santa Lucia, 1998; Owczarzy et al., 1997; Gray, 1997, *Biopolymers* 42: 795-810). The model assumes that interactions contributing significantly to duplex stability are between neighboring nucleotides. Interactions between nucleotides located farther apart are considered to be negligible. In the nearest-neighbor model, enthalpies, entropies and free energies are calculated from parameters representing doublets of two consecutive base pairs. There are 10 doublets for DNA base pairs, 32 doublets for isolated LNA/DNA base pairs and 16 doublets for consecutive LNA/DNA base pairs. The nearest neighbor parameters, $\Delta H_{ij}^{n-n}$, $\Delta S_{ij}^{n-n}$ and $\Delta G_{ij}^{n-n}$ are defined as transition enthalpies, entropies and free energies for these doublets, respectively. Transition enthalpies, $\Delta H^\circ$, entropies, $\Delta S^\circ$, and free energies, $\Delta G^\circ$, for the entire duplex used in equation (1) are calculated by summing thermodynamic parameters, $$\Delta H^\circ = \sum_{i,j=A,C,G,T} N_{ij}^{n-n} \Delta H_{ij}^{n-n} \tag{2}$$

$$\Delta S^\circ = \sum_{i,j=A,C,G,T} N_{ij}^{n-n} \Delta S_{ij}^{n-n} \tag{3}$$

$$\Delta G^\circ = \sum_{i,j=A,C,G,T} N_{ij}^{n-n} \Delta G_{ij}^{n-n} \tag{4}$$

where $N^{n-n}$ is the number of the particular doublets present in the oligonucleotide sequence. The sum on the right sides of equations (2), (3) and (4) are calculated over all kinds of nearest-neighbor doublets (e.g., AA, AC, AG) that are present in the duplex sequence. The invention provides thermodynamic parameters for 16 doublets of matched consecutive LNA/DNA base pairs and 48 doublets of consecutive LNA/DNA base pairs that contain single mismatch. The doublets that represent end interactions of duplex termini (so called initiation enthalpies, entropies and free energies) are also included in summations of equations (2), (3) and (4) (Owczarzy et al., 1997). Persons skilled in art will recognize that $\Delta H_{ij}^{n-n}$, $\Delta S_{ij}^{n-n}$ and $\Delta G_{ij}^{n-n}$ values are related. Nearest-neighbor parameters for free energies could be obtained from enthalpy and entropy parameters.

$$\Delta G_{ij}^{n-n} = \Delta H_{ij}^{n-n} - T\Delta S_{ij}^{n-n}$$

The temperature is denoted T.

Melting temperatures of oligonucleotides containing consecutive LNA modifications are accurately predicted when thermodynamic parameters reported in Table 1 and Table 2 are used in equations (1), (2), (3), and (4). These parameters may be employed in concert with published nearest-neighbor parameters for DNA (Santa Lucia, 1998) and isolated LNA-DNA base pairs (McTigue et al., 2004). Table 1 contains nearest neighbor parameters for doublets of nucleotides where both nucleotides are matched base pairs, i.e., adenine-thymine or guanine-cytosine pairs. Table 2 shows parameters where nearest-neighbor doublet sequence contains one mismatch.

The new parameters of the present invention provide accurate predictions of melting temperature of nucleic acid duplexes in 1M Na$^+$ solution. A person skilled in the biophysics art will recognize that melting temperatures in solutions of different cation concentrations could be predicted from a melting temperature in 1M Na$^+$ by salt correction formulas known in the art (Owczarzy et al., 2004, *Biochemistry* 43: 3537-54; Owczarzy et al., 2008, *Biochemistry* 47(19): 5336-53; U.S. Pat. No. 6,889,143).

Table 1 provides thermodynamic parameters for matched consecutive LNA-DNA base pairs of nucleic acid duplexes. Table 2 provides thermodynamic parameters for mismatches located in consecutive LNA-DNA base pairs of nucleic acid duplexes.

TABLE 1

Thermodynamic parameters for LNA doublets

| 5'/LNA3'/3'DNA5' nearest-neighbors/(ij)$^a$ | $\Delta H_{ij}^{n-n}$ (kcal/mol) | $\Delta S_{ij}^{n-n}$ (cal/(mol · K)) | $\Delta G_{ij}^{n-n}$ (37° C.) (kcal/mol) |
|---|---|---|---|
| +A + A/TT | −9.991 | −27.175 | −1.569 |
| +A + C/TG | −11.389 | −28.963 | −2.435 |
| +A + G/TC | −12.793 | −31.607 | −3.065 |
| +A + T/TA | −14.703 | −40.750 | −2.115 |
| +C + A/GT | −14.177 | −35.498 | −3.107 |
| +C + C/GG | −15.399 | −36.375 | −4.146 |
| +C + G/GC | −14.558 | −35.239 | −3.645 |
| +C + T/GA | −15.737 | −41.218 | −2.919 |
| +G + A/CT | −13.959 | −35.097 | −3.034 |
| +G + C/CG | −16.109 | −40.738 | −3.477 |
| +G + G/CC | −13.022 | −29.673 | −3.821 |
| +G + T/CA | −17.361 | −45.858 | −3.123 |
| +T + A/AT | −10.318 | −26.108 | −2.191 |
| +T + C/AG | −9.166 | −21.535 | −2.478 |
| +T + G/AC | −10.046 | −22.591 | −3.075 |
| +T + T/AA | −10.419 | −27.683 | −1.826 |

$^a$LNA modified nucleotide is denoted "+N".
The +C is 5-methylcytosine LNA nucleotide.

TABLE 2

Thermodynamic parameters for LNA doublets

| 5'/LNA3'/3'DNA5'$^a$ | $\Delta H_{ij}^{n-n}$ (kcal/mol) | $\Delta S_{ij}^{n-n}$ (cal/(mol · K)) | $\Delta G_{ij}^{n-n}$ (37° C.) (kcal/mol) |
|---|---|---|---|
| +A–A mismatch | | | |
| +A + A/A̲T | −3.826 | −13.109 | 0.294 |
| +A + C/A̲G | −2.367 | −7.322 | −0.082 |
| +A + G/A̲C | −4.849 | −13.007 | −0.855 |
| +A + T/A̲A | −5.049 | −17.514 | 0.369 |
| +A +A̲/TA | −4.229 | −15.160 | 0.417 |
| +C +A̲/GA | −5.878 | −17.663 | −0.316 |
| +G +A̲/CA | −8.558 | −23.976 | −1.127 |
| +T +A̲/AA | 2.074 | 3.446 | 1.022 |
| +C–C mismatch | | | |
| +C + A/C̲T | 2.218 | 4.750 | 0.728 |
| +C + C/C̲G | 1.127 | 1.826 | 0.521 |
| +C + G/C̲C | −10.903 | −32.025 | −1.014 |
| +C + T/C̲A | −2.053 | −10.517 | 1.226 |
| +A +C̲/TC | 1.065 | −1.403 | 1.473 |
| +C +C̲/GC | −9.522 | −27.024 | −1.135 |
| +G +C̲/CC | −4.767 | −14.897 | −0.202 |
| +T +C̲/AC | 4.114 | 9.258 | 1.244 |
| +G–G mismatch | | | |
| +G + A/G̲T | −2.920 | −9.387 | 0.018 |
| +G + C/G̲G | −8.139 | −21.784 | −1.414 |
| +G + G/G̲C | −5.149 | −12.508 | −1.326 |
| +G + T/G̲A | −8.991 | −27.311 | −0.510 |
| +A +G̲/TG | −4.980 | −15.426 | −0.241 |
| +C +G̲/GG | −4.441 | −12.158 | −0.672 |
| +G +G̲/CG | −13.505 | −36.021 | −2.347 |
| +T +G̲/AG | −2.775 | −9.286 | 0.108 |
| +T–T mismatch | | | |
| +T + A/T̲T | −3.744 | −12.149 | 0.034 |
| +T + C/T̲G | −4.387 | −13.520 | −0.139 |
| +T + G/T̲C | −6.346 | −16.629 | −1.237 |
| +T + T/T̲A | −7.697 | −25.049 | 0.085 |
| +A +T̲/TT | −4.207 | −14.307 | 0.190 |
| +C +T̲/GT | −8.176 | −22.962 | −1.014 |
| +G +T̲/CT | −7.241 | −20.622 | −0.837 |
| +T +T̲/AT | −2.051 | −7.055 | 0.134 |

TABLE 2-continued

Thermodynamic parameters for LNA doublets

| 5'/LNA3'/3'DNA5'[a] | $\Delta H_{ij}^{n-n}$ (kcal/mol) | $\Delta S_{ij}^{n-n}$ (cal/(mol · K)) | $\Delta G_{ij}^{n-n}$ (37° C.) (kcal/mol) |
|---|---|---|---|
| +A–C mismatch | | | |
| +A + A/CT | −1.362 | −5.551 | 0.383 |
| +A + C/CG | −1.759 | −6.511 | 0.288 |
| +A + G/CC | −6.549 | −18.073 | −0.990 |
| +A + T/CA | −3.563 | −14.105 | 0.806 |
| +A +A/TC | −2.078 | −10.088 | 1.009 |
| +C +A/GC | −5.868 | −16.952 | −0.559 |
| +G +A/CC | −8.477 | −24.565 | −0.855 |
| +T +A/AC | 2.690 | 4.965 | 1.161 |
| +C–A mismatch | | | |
| +C + A/AT | −9.844 | −29.673 | −0.648 |
| +C + C/AG | −3.761 | −11.204 | −0.326 |
| +C + G/AC | −9.845 | −27.316 | −1.418 |
| +C + T/AA | −3.389 | −12.517 | 0.508 |
| +A +C/TA | 0.753 | −0.503 | 0.884 |
| +C +C/GA | −12.714 | −35.555 | −1.680 |
| +G +C/CA | −12.658 | −35.729 | −1.630 |
| +T +C/AA | −1.719 | −7.023 | 0.463 |
| +A–G mismatch | | | |
| +A + A/GT | 2.193 | 4.374 | 0.866 |
| +A + C/GG | −8.453 | −22.672 | −1.434 |
| +A + G/GC | −1.164 | −2.532 | −0.428 |
| +A + T/GA | −7.418 | −24.066 | 0.052 |
| +A +A/TG | −1.963 | −9.013 | 0.797 |
| +C +A/GG | −8.712 | −23.779 | −1.325 |
| +G +A/CG | −7.875 | −21.661 | −1.157 |
| +T +A/AG | 3.207 | 7.156 | 1.010 |
| +G–A mismatch | | | |
| +G + A/AT | −2.914 | −9.402 | 0.018 |
| +G + C/AG | −9.131 | −25.347 | −1.241 |
| +G + G/AC | −2.154 | −3.871 | −1.004 |
| +G + T/AA | −8.515 | −26.313 | −0.354 |
| +A +G/TA | −6.691 | −21.148 | −0.188 |
| +C +G/GA | −3.960 | −10.588 | −0.617 |
| +G +G/CA | −12.898 | −34.656 | −2.158 |
| +T +G/AA | 0.334 | −0.440 | 0.463 |
| +C–T mismatch | | | |
| +C + A/TT | 0.382 | −0.579 | 0.551 |
| +C + C/TG | −2.716 | −8.000 | −0.275 |
| +C + G/TC | −10.363 | −29.315 | −1.316 |
| +C + T/TA | −5.783 | −20.173 | 0.490 |
| +A +C/TT | −0.692 | −5.278 | 0.921 |
| +C +C/GT | −10.299 | −28.503 | −1.455 |
| +G +C/CT | −9.062 | −26.356 | −0.941 |
| +T +C/AT | 2.073 | 3.968 | 0.845 |
| +T–C mismatch | | | |
| +T + A/CT | −5.485 | −17.347 | −0.094 |
| +T + C/CG | 1.451 | 1.556 | 1.023 |
| +T + G/CC | −7.213 | −20.128 | −1.200 |
| +T + T/CA | −2.397 | −11.371 | 1.142 |
| +A +T/TC | −0.633 | −5.801 | 1.125 |
| +C +T/GC | −6.868 | −21.000 | −0.315 |
| +G +T/CC | −5.853 | −16.643 | −0.684 |
| +T +T/AC | 0.211 | −1.446 | 0.656 |
| +G–T mismatch | | | |
| +G + A/TT | −5.551 | −15.398 | −0.759 |
| +G + C/TG | −14.943 | −40.148 | −2.461 |
| +G + G/TC | −8.110 | −18.349 | −2.470 |
| +G + T/TA | −14.213 | −40.041 | −1.795 |
| +A +G/TT | −7.130 | −20.786 | −0.739 |
| +C +G/GT | −14.862 | −39.430 | −2.575 |
| +G +G/CT | −14.622 | −37.510 | −2.997 |
| +T +G/AT | −6.703 | −18.111 | −1.094 |
| +T–G mismatch | | | |
| +T + A/GT | −4.612 | −14.039 | −0.230 |
| +T + C/GG | −9.798 | −26.406 | −1.616 |
| +T + G/GC | −4.519 | −11.065 | −1.132 |
| +T + T/GA | −4.523 | −15.693 | 0.359 |
| +A +T/TG | −2.364 | −8.834 | 0.318 |
| +C +T/GG | −11.396 | −30.732 | −1.852 |
| +G +T/CG | −6.233 | −15.933 | −1.291 |
| +T +T/AG | −2.960 | −9.305 | −0.065 |

[a]LNA modified nucleotide is denoted "+N".
Mismatched bases are underlined.

A person skilled in the biophysics art will recognize that alternative formulas could be employed to predict $\Delta H°$, $\Delta S°$ and $\Delta G°$ values that yield predictions equivalent to predictions obtained from equations (2), (3) and (4), $$\Delta H° = \Delta H°_{DNA} + \Delta\Delta H°_{LNA} \quad (5)$$

$$\Delta S° = \Delta S°_{DNA} + \Delta\Delta S°_{LNA} \quad (6)$$

$$\Delta G° = \Delta G°_{DNA} + \Delta\Delta G°_{LNA} \quad (7)$$

where $\Delta H°_{DNA}$, $\Delta S°_{DNA}$ and $\Delta G°_{DNA}$ are the transition enthalpy, entropy and free energy of unmodified, perfectly matched DNA sequence, respectively. These values could be experimentally measured or predicted using nearest-neighbor parameters for unmodified DNA oligonucleotides (see, e.g., Santa Lucia, 1998; Owczarzy, 1997; Santa Lucia and Hicks, 2004, *Annu. Rev. Biophys. Biomol. Struct.* 33: 415-40). To account for thermodynamic effects of LNA modifications and mismatches, adjustments of enthalpy $\Delta\Delta H°_{LNA}$, entropy $\Delta\Delta H°_{LNA}$ and free energy $\Delta\Delta G°_{LNA}$ are added in equations (5), (6), and (7). These adjustments may also be calculated in terms of nearest-neighbor model, $$\Delta\Delta H°_{LNA} = \sum_{i,j=A,C,G,T} N_{ij}^{n-n} \Delta\Delta H_{ij}^{n-n} \quad (8)$$

$$\Delta\Delta S°_{LNA} = \sum_{i,j=A,C,G,T} N_{ij}^{n-n} \Delta\Delta S_{ij}^{n-n} \quad (9)$$

$$\Delta\Delta G°_{LNA} = \sum_{i,j=A,C,G,T} N_{ij}^{n-n} \Delta\Delta G_{ij}^{n-n} \quad (10)$$

The present invention provides values of $\Delta\Delta H°_{LNA}$, $\Delta\Delta S°_{LNA}$ and $\Delta\Delta G°_{LNA}$ that yield accurate predictions for consecutive LNA modifications. Table 3 shows thermodynamic nearest-neighbor parameters for the difference between LNA-DNA and unmodified DNA-DNA base pairs of the same sequence in nucleic acid duplexes. Table 4 shows thermodynamic nearest-neighbor parameters for the differences between mismatched LNA-DNA base pairs and unmodified, perfectly matched DNA-DNA base pairs in nucleic acid duplexes. Total $\Delta H°$, $\Delta S°$ and $\Delta G°$ values calculated using parameters in Tables 1 and 2 agree with values calculated using parameters in Tables 3 and 4 for any oligonucleotide sequence.

TABLE 3

| Sequence[a] | $\Delta\Delta H_{ij}^{n-n}$ (kcal/mol) | $\Delta\Delta S_{ij}^{n-n}$ (cal/(mol·K)) | $\Delta\Delta G_{ij}^{n-n}$ (37° C.) (kcal/mol) |
|---|---|---|---|
| +A + A/TT | -2.091 | -4.975 | -0.569 |
| +A + C/TG | -2.989 | -6.563 | -0.995 |
| +A + G/TC | -4.993 | -10.607 | -1.785 |
| +A + T/TA | -7.503 | -20.350 | -1.235 |
| +C + A/GT | -5.677 | -12.798 | -1.657 |
| +C + C/GG | -7.399 | -16.475 | -2.306 |
| +C + G/GC | -3.958 | -8.039 | -1.475 |
| +C + T/GA | -7.937 | -20.218 | -1.639 |
| +G + A/CT | -5.759 | -12.897 | -1.734 |
| +G + C/CG | -6.309 | -16.338 | -1.237 |
| +G + G/CC | -5.022 | -9.773 | -1.981 |
| +G + T/CA | -8.961 | -23.458 | -1.683 |
| +T + A/AT | -3.118 | -4.808 | -1.611 |
| +T + C/AG | -0.966 | 0.665 | -1.178 |
| +T + G/AC | -1.546 | 0.109 | -1.625 |
| +T + T/AA | -2.519 | -5.483 | -0.826 |

[a] Symbol +N indicates LNA nucleotide. +C is 5-methyl cytosine LNA.
Nearest-neighbor sequence direction is 5'-3'/3'-5'

TABLE 4

| 5'LNA3'/3'DNA5'[a] | $\Delta\Delta H_{ij}^{n-n}$ (kcal/mol) | $\Delta\Delta S_{ij}^{n-n}$ (cal/(mol·K)) | $\Delta\Delta G_{ij}^{n-n}$ (37° C.) (kcal/mol) |
|---|---|---|---|
| +A–A mismatch | | | |
| +A + A/AT | 4.074 | 9.091 | 1.294 |
| +A + C/AG | 6.033 | 15.078 | 1.358 |
| +A + G/AC | 2.951 | 7.993 | 0.425 |
| +A + T/AA | 2.151 | 2.886 | 1.249 |
| +A +A/TA | 3.671 | 7.040 | 1.417 |
| +C +A/GA | 2.622 | 5.037 | 1.134 |
| +G +A/CA | -0.358 | -1.776 | 0.173 |
| +T +A/AA | 9.274 | 24.746 | 1.602 |
| +C–C mismatch | | | |
| +C + A/CT | 10.718 | 27.450 | 2.178 |
| +C + C/CG | 9.127 | 21.726 | 2.361 |
| +C + G/CC | -0.303 | -4.825 | 1.156 |
| +C + T/CA | 5.747 | 10.483 | 2.506 |
| +A +C/TC | 9.465 | 20.997 | 2.913 |
| +C +C/GC | -1.522 | -7.124 | 0.705 |
| +G +C/CC | 5.033 | 9.503 | 2.038 |
| +T +C/AC | 12.314 | 31.458 | 2.544 |
| +G–G mismatch | | | |
| +G + A/GT | 5.280 | 12.813 | 1.318 |
| +G + C/GG | 1.661 | 2.616 | 0.826 |
| +G + G/GC | 2.851 | 7.392 | 0.514 |
| +G + T/GA | -0.591 | -4.911 | 0.930 |
| +A +G/TG | 2.820 | 5.574 | 1.039 |
| +C +G/GG | 6.159 | 15.042 | 1.498 |
| +G +G/CG | -5.505 | -16.121 | -0.507 |
| +T +G/AG | 5.725 | 13.414 | 1.558 |
| +T–T mismatch | | | |
| +T + A/TT | 3.456 | 9.151 | 0.614 |
| +T + C/TG | 3.813 | 8.680 | 1.161 |
| +T + G/TC | 2.154 | 6.071 | 0.213 |
| +T + T/TA | 0.203 | -2.849 | 1.085 |
| +A +T/TT | 2.993 | 6.093 | 1.070 |
| +C +T/GT | -0.376 | -1.962 | 0.266 |
| +G +T/CT | 1.159 | 1.778 | 0.603 |
| +T +T/AT | 5.849 | 15.145 | 1.134 |
| +A–C mismatch | | | |
| +A + A/CT | 6.538 | 16.649 | 1.383 |
| +A + C/CG | 6.641 | 15.889 | 1.728 |
| +A + G/CC | 1.251 | 2.927 | 0.290 |
| +A + T/CA | 3.637 | 6.295 | 1.686 |
| +A +A/TC | 5.822 | 12.112 | 2.009 |
| +C +A/GC | 2.632 | 5.748 | 0.891 |
| +G +A/CC | -0.277 | -2.365 | 0.445 |
| +T +A/AC | 9.890 | 26.265 | 1.741 |
| +C–A mismatch | | | |
| +C + A/AT | -1.344 | -6.973 | 0.802 |
| +C + C/AG | 4.239 | 8.696 | 1.514 |
| +C + G/AC | 0.755 | -0.116 | 0.752 |
| +C + T/AA | 4.411 | 8.483 | 1.788 |
| +A +C/TA | 9.153 | 21.897 | 2.324 |
| +C +C/GA | -4.714 | -15.655 | 0.160 |
| +G +C/CA | -2.858 | -11.329 | 0.610 |
| +T +C/AA | 6.481 | 15.177 | 1.763 |
| +A–G mismatch | | | |
| +A + A/GT | 10.093 | 26.574 | 1.866 |
| +A + C/GG | -0.053 | -0.272 | 0.006 |
| +A + G/GC | 6.636 | 18.468 | 0.852 |
| +A + T/GA | -0.218 | -3.666 | 0.932 |
| +A +A/TG | 5.937 | 13.187 | 1.797 |
| +C +A/GG | -0.212 | -1.079 | 0.125 |
| +G +A/CG | 0.325 | 0.539 | 0.143 |
| +T +A/AG | 10.407 | 28.456 | 1.590 |
| +G–A mismatch | | | |
| +G + A/AT | 5.286 | 12.798 | 1.318 |
| +G + C/AG | 0.669 | -0.947 | 0.999 |
| +G + G/AC | 5.846 | 16.029 | 0.836 |
| +G + T/AA | -0.115 | -3.913 | 1.086 |
| +A +G/TA | 1.109 | -0.148 | 1.092 |
| +C +G/GA | 6.640 | 16.612 | 1.553 |
| +G +G/CA | -4.898 | -14.756 | -0.318 |
| +T +G/AA | 8.834 | 22.260 | 1.913 |
| +C–T mismatch | | | |
| +C + A/TT | 8.882 | 22.121 | 2.001 |
| +C + C/TG | 5.284 | 11.900 | 1.565 |
| +C + G/TC | 0.237 | -2.115 | 0.854 |
| +C + T/TA | 2.017 | 0.827 | 1.770 |
| +A +C/TT | 7.708 | 17.122 | 2.361 |
| +C +C/GT | -2.299 | -8.603 | 0.385 |
| +G +C/CT | 0.738 | -1.956 | 1.299 |
| +T +C/AT | 10.273 | 26.168 | 2.145 |
| +T–C mismatch | | | |
| +T + A/CT | 1.715 | 3.953 | 0.486 |
| +T + C/CG | 9.651 | 23.756 | 2.323 |
| +T + G/CC | 1.287 | 2.572 | 0.430 |
| +T + T/CA | 5.503 | 10.829 | 2.142 |
| +A +T/TC | 6.567 | 14.599 | 2.005 |
| +C +T/GC | 0.932 | 0.000 | 0.965 |
| +G +T/CC | 2.547 | 5.757 | 0.756 |
| +T +T/AC | 8.111 | 20.754 | 1.656 |

TABLE 4-continued

| 5'LNA3'/3'DNA5'[a] | $\Delta\Delta\ H_{ij}^{n-n}$ (kcal/mol) | $\Delta\Delta\ S_{ij}^{n-n}$ (cal/(mol · K)) | $\Delta\Delta\ G_{ij}^{n-n}$ (37° C.) (kcal/mol) |
|---|---|---|---|
| +G—T mismatch | | | |
| +G + A/TT | 2.649 | 6.802 | 0.541 |
| +G + C/TG | −5.143 | −15.748 | −0.221 |
| +G + G/TC | −0.110 | 1.551 | −0.630 |
| +G + T/TA | −5.813 | −17.641 | −0.355 |
| +A +G/TT | 0.670 | 0.214 | 0.541 |
| +C +G/GT | −4.262 | −12.230 | −0.405 |
| +G +G/CT | −6.622 | −17.610 | −1.157 |
| +T +G/AT | 1.797 | 4.589 | 0.356 |
| +T—G mismatch | | | |
| +T + A/GT | 2.588 | 7.261 | 0.350 |
| +T + C/GG | −1.598 | −4.206 | −0.316 |
| +T + G/GC | 3.981 | 11.635 | 0.318 |
| +T + T/GA | 3.377 | 6.507 | 1.359 |
| +A +T/TG | 4.836 | 11.566 | 1.198 |
| +C +T/GG | −3.596 | −9.732 | −0.572 |
| +G +T/CG | 2.167 | 6.467 | 0.149 |
| +T +T/AG | 4.940 | 12.895 | 0.935 |

[a]LNA modified nucleotide is denoted "+N".
Mismatched bases are underlined.
The +C is 5-methylcytosine LNA nucleotide.

In one embodiment, the methods of the present invention can be used to design LNA-modified fluorescence-quenched oligonucleotide probes to distinguish single nucleotide polymorphisms (SNPs) using the 5'-nuclease assay in qPCR. Single nucleotide polymorphisms represent a primary source of variation between individuals, and specific genotypes are associated with a variety of disease states. The ability to specifically distinguish between different genotypes is a common need and a variety of molecular genetics assay formats have been devised to detect SNPs. One commonly employed assay links quantitative PCR (qPCR) with allele-specific fluorescence-quenched hybridization probes. PCR enables detection of specific nucleic acid sequences from minute amounts of input genomic DNA. The hybridization probe is specific for the SNP sequence, such that a probe specific to allele A will hybridize only to allele A and not to allele B at the reaction temperature. Similarly a probe specific to allele B will hybridize only to allele B and not to allele A at the reaction temperature. Probes of this type are commonly used in a fluorescence-quenched assay format wherein each probe has a reporter fluorescent dye at one end and a quencher at the other end. When intact, the reporter dye and the quencher are in proximity and little fluorescence is detectable (i.e., the probe is "dark"). During PCR, the 5'-exonuclease activity of the DNA polymerase degrades the probe (5'-hydrolysis assay format) which is positioned between the forward and reverse primers; probe degradation separates reporter and quencher, resulting in a detectable increase in fluorescence signal (i.e., the probe becomes "bright"). If each probe is labeled with a different dye, both probes to be used simultaneously in a single tube multiplex reaction and the results tracked by following the unique spectral emission of each dye. For example, the allele A probe can be tagged with the dye FAM (emission 520 nm) and the allele B probe can be tagged with the dye HEX (emission 556 nm). The spectral signatures of these two dyes are easily distinguishable permitting multiplex reactions to be performed with both dyes present.

When SNP genotyping assays are performed in this format, it is essential that the probes uniquely hybridize to their specific targets. Hybridization is influenced by the reaction temperature and buffer conditions. Typically qPCR reactions are performed at or around 60° C. in a buffer containing 20 mM Tris pH 8.3, 50 mM KCl, 3 mM MgCl$_2$, 800 µM dNTPs, 200-500 nM primers, and 200-300 nM probe. Other buffers can be used, but qPCR buffers generally have a final ionic content similar to this recipe. Under these conditions, the A allele probe should hybridize to A allele DNA but not B allele DNA. Similarly the B allele probe should hybridize to B allele DNA but not A allele DNA. While this requirement appears straightforward, in practice it is often difficult to design probe oligonucleotides that meet these criteria. Frequently probes do not show a sufficient difference between their $T_m$ for match vs. mismatch targets and as a result some level of cross-reactivity occurs during PCR and the genotype of the DNAs being studied cannot be reliably called.

Incorporation of chemical modifying groups in the probes which increase $T_m$, such as LNA bases, allows for use of shorter probes and increases the $\Delta T_m$ between match and mismatch, improving the accuracy of the genotyping assay. Unfortunately, thermodynamic parameters and predictive algorithms heretofore did not exist that permitted sufficiently accurate prediction of the $T_m$ of LNA modified oligonucleotides to aid in design of probes that bind to perfectly matched target nucleic acids but do not bind to mismatched targets. As a result, it was usually necessary to design a series of probes having subtle variations in length and position relative to the SNP base and empirically test these experimentally. This essentially is a "trial and error" method to obtain probes capable of SNP discrimination and can be both costly and time consuming.

The present invention comprises a set of experimentally determined thermodynamic parameters for LNA bases that can be employed in an algorithm to accurately predict $T_m$ of synthetic oligonucleotide probes. The oligonucleotides can contain a single LNA base or multiple LNA bases. The LNA bases can be dispersed throughout the sequence or can be adjacent. The predictive algorithm can be used to estimate $T_m$ for both hybridization to perfect match targets or targets having a mismatch, which in the case of the present example represents the SNP site. The algorithm is used in the method of the present invention to design probe oligonucleotides having a desired $T_m$ with greater accuracy than was previously possible. Probe designs obtained using the new method typically show the desired level of match vs. mismatch selectivity, eliminating the need for the repeated cycles of probe-re-design, synthesis, and testing which was expected in the historical approach to this problem which relied upon less accurate predictive models followed by trial and error empiric testing.

The term "locked nucleic acids" (LNA's) refer to RNA modifications with a bicyclic structure wherein a bridge connects two points of an RNA monomer, typically locking the ribose in an A-form conformation. One example is wherein a methyl bridge connects the 2'-oxygen and the 4'-carbon of the RNA (see U.S. Pat. Nos. 6,734,291 and 6,794,499). Positions of the RNA or on the bridge can be modified with additional groups, such as an additional methyl group on the bridge (see U.S. Pat. Nos. 7,741,457 and 7,569,686).

The following examples further illustrate the invention but should not be construed as in any way limiting its scope.

EXAMPLE 1

This example demonstrates use of the invention in a systematic melting study of 53 oligonucleotides that contain two consecutive LNA modifications. These LNA duplexes ranged from 8 to 10 base pairs in lengths, from 10% to 88% in G·C contents and from 20% to 60% in LNA contents. The oligonucleotides did not have any fluorescent labels or quenchers attached. Melting profiles of these DNA duplexes were experimentally measured in 1M Na⁺ solution.

DNA and LNA oligomers were synthesized on solid supports using phosphoramidite chemistry and purified using high-pressure liquid chromatography or polyacrylamide gel electrophoresis. Published procedures were followed (Moreira et al., 2005, *Biochem. Biophys. Res. Commun.* 327: 473-84; Owczarzy et al., 2004). The capillary electrophoresis assay carried out on Beckman PACE 5000 system indicated that all oligomers were more than 90% pure. Molar masses of oligomers were determined on ESI-LCMS Oligo HTCS system. Experimental molar masses of all oligomers were within 4 g/mol of expected molar masses. Concentrations of DNA oligomers were determined from absorbance at 260 nm and estimated extinction coefficients, which were calculated using the nearest-neighbor model (1 HANDBOOK OF BIOCHEMISTRY AND MOLECULAR BIOLOGY 589 (Gerald D. Fasman, ed., CRC Press, Inc. 1975). It was assumed that LNA modifications do not significantly change the extinction coefficient (You et al., 2006; McTigue et al., 2004). Each oligonucleotide was mixed with its complementary DNA strand in 1:1 molar ratio, heated to 95° C., slowly cooled down to an ambient temperature and diluted to single strand DNA concentration of 4 μM.

Melting profiles were collected in a 1M Na⁺ buffer consisting of 1M NaCl, 10 mM sodium phosphate, 1 mM Na₂EDTA (Owczarzy et al., 2004). The pH was adjusted to 7 (at 25° C.) with 1M NaOH. Absorbance values at 268 nm were recorded every 0.1° C. in the temperature range of 10-99° C. on a single beam Beckman DU 650 spectrophotometer (Beckman-Coulter) with a Micro Tm Analysis accessory and Beckman High Performance Peltier Controller. Cuvettes of 1 cm pathlength were heated at a rate of (24.9±0.3)° C./hour. Both heating (denaturation) and cooling (renaturation) experiments were measured for each DNA sample in at least two different cuvettes to minimize systematic errors. Melting profiles of buffers alone were also measured in the same cuvettes and subtracted digitally from melting profiles of DNA samples. Experiments were analyzed as described earlier (Owczarzy et al., 2004). The fraction of melted base pairs, θ, was calculated from the graph of absorbance vs. temperature. Melting temperatures were read as temperatures where θ=0.5 and were reproducible within 0.3° C. All melting curves showed single S-shaped transitions. Denaturation and renaturation melting profiles were superimposable indicating equilibrium conditions.

Figure 6:
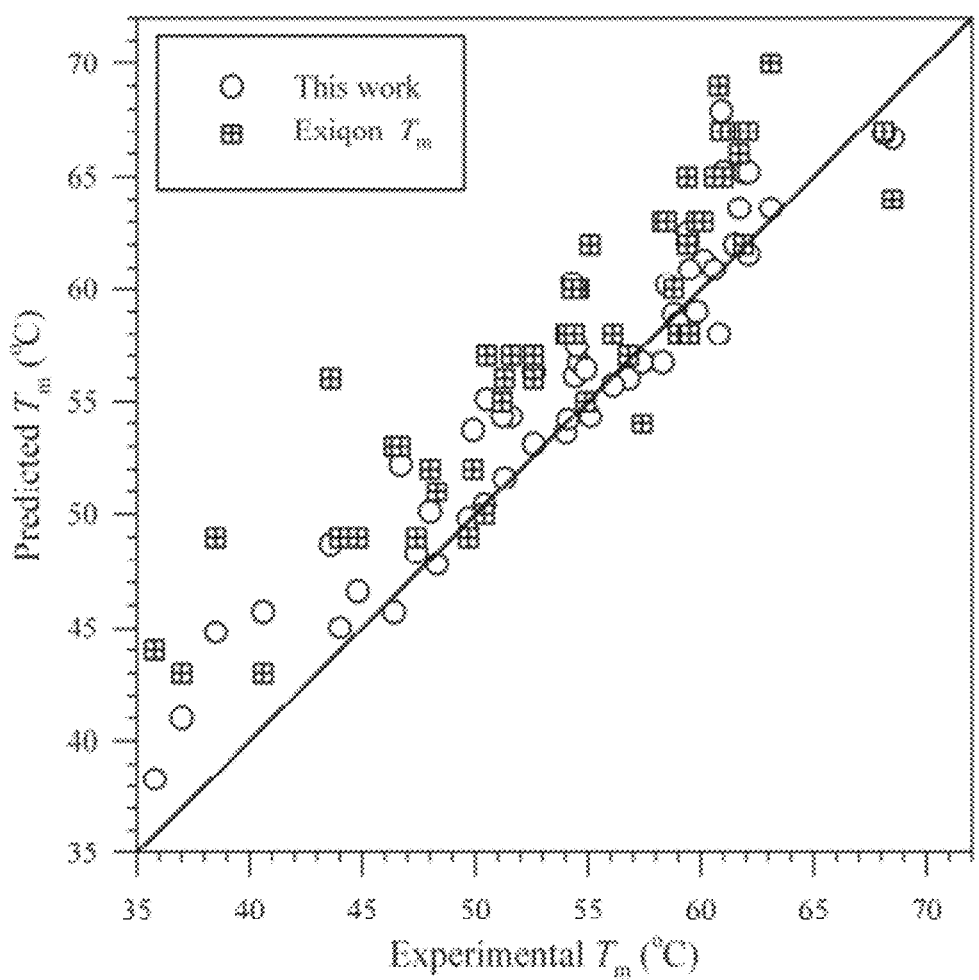
FIG. 6 presents a comparison of experimentally measured melting temperatures with predictions. Associated data are shown in Table 5.

Melting temperatures were predicted using parameters in Table 1 and equations (1), (2), and (3). These predicted $T_m$ values were compared with experimentally measured values. Comparisons are presented in Table 5, which shows measured and predicted melting temperatures of 53 LNA-DNA duplex oligonucleotides in 1M Na⁺ solution. LNA modified nucleotide is denoted "+N". FIG. 6 presents a comparison of experimentally measured melting temperatures with predictions. The parameters in Table 1 result in an average $T_m$ prediction error of 2.1° C. ($\chi^2$=2549). The difference between predicted and measured $T_m$ was calculated for each sequence and is shown in the last column of Table 5. The average absolute value of these differences, i.e., average error of $T_m$ prediction, over the entire set of 32 duplexes is 1.6° C. The similar error of $T_m$ predictions (±1.5° C.) is observed for nearest-neighbor model of unmodified DNA oligonucleotides (See Table VII of Owczarzy, et. al., 1997). This result demonstrates that nearest-neighbor model predicts accurately melting temperatures of oligonucleotides that contain consecutive LNA modifications.

TABLE 5

| Sequence ID | Sequence (5' to 3') | LNA % | Experimental $T_m$ [° C.]ᵃ | Predicted $T_m$ [° C.] | $T_m$ prediction error [° C.] |
|---|---|---|---|---|---|
| VAL-01 | CCG + A + AGCC | 25% | 51.3 | 51.6 | 0.3 |
| VAL-02 | CCG + A + CGCC | 25% | 59.8 | 59.0 | -0.8 |
| VAL-03 | CCG + A + GGCC | 25% | 62.1 | 61.6 | -0.5 |
| VAL-04 | CCG + A + TGCC | 25% | 54.0 | 53.6 | -0.4 |
| VAL-05 | CCG + C + AGCC | 25% | 61.7 | 63.6 | 1.9 |
| VAL-06 | CAG + C + CGTC | 25% | 58.8 | 58.9 | 0.1 |
| VAL-07 | CTG + C + GGAC | 25% | 58.3 | 56.7 | -1.6 |
| VAL-08 | CCG + C + TGCC | 25% | 61.5 | 62.0 | 0.5 |
| VAL-09 | CCG + G + AGCC | 25% | 59.4 | 62.1 | 2.7 |
| VAL-10 | CTG + G + CGAC | 25% | 54.1 | 54.2 | 0.1 |
| VAL-11 | CCG + G + TGCC | 25% | 60.1 | 61.3 | 1.2 |
| VAL-12 | CCG + T + AGCC | 25% | 56.8 | 56.0 | -0.8 |
| VAL-13 | CCG + T + CGCC | 25% | 60.6 | 60.9 | 0.3 |
| VAL-14 | CCG + T + GGCC | 25% | 63.1 | 63.6 | 0.5 |
| VAL-15 | CCG + T + TGCC | 25% | 55.1 | 54.3 | -0.8 |
| VAL-16 | GGA + A + ACGC | 25% | 44.0 | 45.0 | 1.0 |
| VAL-17 | GGA + A + CCGC | 25% | 52.6 | 53.1 | 0.5 |

TABLE 5-continued

| Sequence ID | Sequence (5' to 3') | LNA % | Experimental $T_m$ [° C.][a] | Predicted $T_m$ [° C.] | $T_m$ prediction error [° C.] |
|---|---|---|---|---|---|
| VAL-18 | GGA + A + GCGC | 25% | 52.6 | 56.3 | 3.7 |
| VAL-19 | GGA + A + TCGC | 25% | 44.8 | 46.6 | 1.8 |
| VAL-20 | GGA + C + ACGC | 25% | 54.4 | 56.1 | 1.7 |
| VAL-21 | GGA + C + CCGC | 25% | 61.0 | 65.2 | 4.2 |
| VAL-22 | GGA + C + GCAC | 25% | 56.1 | 55.7 | -0.4 |
| VAL-23 | GGA + C + TCGC | 25% | 51.6 | 54.3 | 2.7 |
| VAL-24 | GGA + G + ACGC | 25% | 50.5 | 55.1 | 4.6 |
| VAL-25 | GGA + G + CCGC | 25% | 58.5 | 60.2 | 1.7 |
| VAL-26 | CGT + G + GTAG | 25% | 48.3 | 47.8 | -0.5 |
| VAL-27 | ACA + G + GAGT | 25% | 48.0 | 50.1 | 2.1 |
| VAL-28 | GGA + G + TCGC | 25% | 51.2 | 54.3 | 3.1 |
| VAL-29 | GGA + T + ACGC | 25% | 47.4 | 48.3 | 0.9 |
| VAL-30 | GCA + T + CCGC | 25% | 54.6 | 56.7 | 2.1 |
| VAL-31 | GGA + T + GCGC | 25% | 54.5 | 57.4 | 2.9 |
| VAL-32 | GGA + T + TCGC | 25% | 46.4 | 45.7 | -0.7 |
| VAL-33 | ATCT + T + TTTCA | 20% | 37.0 | 41.0 | 4.0 |
| VAL-34 | ATC + A + A + A + ATTA | 40% | 35.8 | 38.3 | 2.5 |
| VAL-35 | ATC + T + T + T + TTCA | 40% | 43.6 | 48.7 | 5.1 |
| VAL-36 | ATC + A + T + A + TTTA | 40% | 40.6 | 45.7 | 5.1 |
| VAL-37 | ATC + C + G + C + GTTA | 40% | 60.9 | 67.9 | 7.0 |
| VAL-38 | TAC + G + A + G + ATTA | 40% | 59.0 | 58.5 | -0.5 |
| VAL-39 | TAC + T + C + T + CTTA | 40% | 57.4 | 56.7 | -0.7 |
| VAL-40 | ATC + A + C + A + CTTA | 40% | 54.9 | 56.4 | 1.5 |
| VAL-41 | ATC + T + G + T + GTTA | 40% | 59.5 | 60.9 | 1.4 |
| VAL-42 | ATC + C + A + G + CTTA | 40% | 61.9 | 65.2 | 3.3 |
| VAL-43 | ATC + G + T + A + ATAT | 40% | 49.7 | 49.8 | 0.1 |
| VAL-44 | ATC + T + G + G + CTTA | 40% | 68.5 | 66.7 | -1.8 |
| VAL-45 | ATC + C + C + T + TAAT | 40% | 54.3 | 60.3 | 6.0 |
| VAL-46 | TAC + A + T + C + ATTA | 40% | 50.4 | 50.4 | 0.0 |
| VAL-47 | ATC + T + T + G + TTTA | 40% | 49.9 | 53.7 | 3.8 |
| VAL-48 | ATC + G + G + G + TTAC | 40% | 68.1 | 66.9 | -1.2 |
| VAL-49 | ATCT + T + T + TTCA | 30% | 38.5 | 44.8 | 6.3 |
| VAL-50 | AT + C + T + T + T + T + TCA | 60% | 60.8 | 58.0 | -2.8 |
| VAL-51 | A + T + CTTT + T + TCA | 40% | 46.7 | 52.2 | 5.5 |
| VAL-52 | GGA + A + C + CGC | 38% | 59.4 | 62.5 | 3.1 |
| VAL-53 | GG + A + A + C + CGC | 50% | 62.1 | 65.2 | 3.1 |

EXAMPLE 2

One embodiment of the invention is also shown for LNA oligonucleotides that hybridize to DNA oligonucleotides that are not perfectly complementary. Those oligonucleotides form LNA-DNA duplexes containing mismatched base pairs. We have studied a set of 7 unique base sequences. Unmodified DNA oligonucleotides and LNA modified oligonucleotides of the same base sequence were synthesized and their melting temperatures were measured. Experimental procedures that are reported in Example 1 were followed to obtain experimental melting temperatures. Various mismatches (C-A, G-T, A-C, C-C, A-G, T-C) were introduced in the middle of three consecutive LNA nucleotides. Table 6 shows experimentally measured and predicted melting temperatures. LNA modifications were predicted to have negative impact on mismatch discrimination, $\Delta T_m$ (° C.), for the first two sequences (VAL-A and VAL-B). Mismatch discrimination in the next two sequences (Val-C and VAL-D) was predicted to be negligibly influenced by LNA modifications. Significant improvements in mismatch discrimination were forecast for the last three sequence sets (VAL-E, VAL-F, VAL-G). The $T_m$ predictions are in agreement with experimentally measured values. This result confirms utility and accuracy of parameters reported in Tables 1 and 2. Table 6 shows a comparison of predicted and measured mismatch discrimination for LNA oligonucleotides

TABLE 6

| Sequence ID | Sequence (5' to 3') | Mismatch | LNA site | Exper. $T_m$ (° C.) | Predicted $T_m$ (° C.) | Exper. $\Delta T_m$ (° C.)[b] | Predicted $\Delta T_m$ (° C.) |
|---|---|---|---|---|---|---|---|
| VAL-A1 | TGACGGAGCGATTCAGC | None | None | 70.5 | 72.2 | — | — |
| VAL-A2 | TGACGGAGCGATTCAGC | C - A | None | 58.5 | 60.9 | -12.0 | -11.3 |
| VAL-A3 | TGACGGA + G + C + GATTCAGC | None | +G + C + G/CGC | 78.6 | 79.3 | — | — |
| VAL-A4 | TGACGGA + G + C + GATTCAGC | +C - A | +G + C + G/CAC | 68.5 | 70.1 | -10.1 | -9.2 |
| VAL-B1 | CTATCCAGGCATTCGCA | None | None | 67.4 | 69.1 | — | — |
| VAL-B2 | CTATCCAGGCATTCGCA | G - T | None | 61.1 | 62.7 | -6.3 | -6.4 |
| VAL-B3 | CTATCCA + G + G + CATTCGCA | None | +G + G + C/CCG | 77.4 | 77.5 | — | — |
| VAL-B4 | CTATCCA + G + G + CATTCGCA | +G - T | +G + G + C/CTG | 70.7 | 72.4 | -6.7 | -5.1 |
| VAL-C1 | TTACTGTCAAGGCAACT | None | None | 64.3 | 65.4 | — | — |
| VAL-C2 | TTACTGTCAAGGCAACT | A - C | None | 52.6 | 56.9 | -11.7 | -8.5 |
| VAL-C3 | TTACTGT + C + A + AGGCAACT | None | +C + A + A/GTT | 73.0 | 72.8 | — | — |
| VAL-C4 | TTACTGT + C + A + AGGCAACT | +A - C | +C + A + A/GCT | 61.4 | 64.0 | -11.6 | -8.8 |
| VAL-D1 | GCGTCAAGCGACATCAT | None | None | 69.2 | 70.3 | — | — |
| VAL-D2 | GCGTCAAGCGACATCAT | C - C | None | 52.3 | 58.0 | -16.9 | -12.3 |
| VAL-D3 | GCGTCAA + G + C + GACATCAT | None | +G + C + G/CGC | 75.0 | 77.5 | — | — |
| VAL-D4 | GCGTCAA + G + C + GACATCAT | +C - C | +G + C + G/CGC | 57.4 | 64.8 | -17.6 | -12.7 |
| VAL-E1 | CGACTTGTCCATACCTA | None | None | 64.7 | 64.6 | — | — |
| VAL-E2 | CGACTTGTCCATACCTA | C - C | None | 50.5 | 54.5 | -14.2 | -10.1 |
| VAL-E3 | CGACTTG + T + C + CATACCTA | None | +T + C + C/AGG | 73.7 | 74.7 | — | — |
| VAL-E4 | CGACTTG + T + C + CATACCTA | +C - C | +T + C + C/AGG | 53.6 | 56.6 | -20.1 | -18.1 |
| VAL-F1 | CCATGCGTAGACAAGTG | None | None | 65.3 | 67.4 | — | — |
| VAL-F2 | CCATGCGTAGACAAGTG | A - G | None | 61.0 | 63.1 | -4.3 | -4.3 |
| VAL-F3 | CCATGCG + T + A + GACAAGTG | None | + T + A + G/ATC | 74.4 | 77.0 | — | — |
| VAL-F4 | CCATGCG + T + A + GACAAGTG | +A - G | +T + A + G/AGC | 65.6 | 67.0 | -8.8 | -10.0 |

TABLE 6-continued

| Sequence ID | Sequence (5' to 3') | Mismatch | LNA site | Exper. $T_m$ (° C.) | Predicted $T_m$ (° C.) | Exper. $\Delta T_m$ (° C.)[b] | Predicted $\Delta T_m$ (° C.) |
|---|---|---|---|---|---|---|---|
| VAL-G1 | CTATCGCATCTAATAAT | None | None | 58.1 | 56.6 | — | — |
| VAL-G2 | CTATCGCATCTAATAAT | T—C | None | 48.0 | 48.6 | -10.1 | -8.0 |
| VAL-G3 | CTATCGC + A + T + CTAATAAT | None | +A + T + C/TAG | 63.8 | 63.6 | — | — |
| VAL-G4 | CTATCGC + A + T + CTAATAAT | +T — C | +A + T + C/TCG | 50.6 | 48.1 | -13.2 | -15.5 |

[a]Total single-strand concentrations, $C_t$, were 2 ± 0.2 μM.
[b]The difference between melting temperature of single base mismatched and perfectly matched duplex.

EXAMPLE 3

The present Example demonstrates shows use of the methods of the present invention to design LNA-modified fluorescence-quenched oligonucleotide probes to distinguish single nucleotide polymorphisms (SNPs) using the 5'-nuclease assay in qPCR, specifically the use of the probe design method of the present invention to distinguish between a "C" allele vs. a "T" allele in the mouse Leptin gene (GenBank Acc. No. NM_008493). The sequence of the mouse Leptin gene is shown below spanning the site of the C/T SNP of interest. Binding sites for the forward primer, reverse primer, and probes are underlined. The site of the SNP is indicated (C/T).

CACCAGCCTGCCTTCCCAAAATGTGCTGCAGATAGCCAATGACCTG

GAGAATCTC(C/T)GAGACCTCCTCCATCTGCTGGCCTTCTCCAAG

AGCTGCTCCCTG

Primers were design to amplify this locus using standard design criteria, as are well known to those with skill in the art. The forward and reverse primers flank the SNP site as indicated above. Probe oligonucleotides had LNA bases placed at the position of the SNP base and at the positions immediately 5'- and 3'-to the SNP according to criteria taught by You et al., 2006. Probe oligonucleotides were designed using the $T_m$ algorithm with new LNA parameters (see Examples 1 and 2 above) using the method of the present invention. Probes were designed to optimize the $T_m$ differential ($\Delta T_m$) between match and mismatch for annealing at 60° C. under the buffer conditions specified above. Primers and probes for Leptin SNP qPCR are shown in Table 7 below.

The new algorithm permitted rapid design of probes where the reaction temperature of 60° C. lies halfway between the values for "$T_m$ Match" and the "$T_m$ Mismatch" for both probes. The predicted $\Delta T_m$ was larger for the "C" probe (C:G match vs. C:A mismatch) compared with the "T" probe (T:A match vs. T:G mismatch). This is expected since the T:G mismatch pair is relatively stable compared with other mismatch pairs. If the method of the present invention was successful, then the probe designs indicated in Table 7 should work well to distinguish the "C" and "T" genotypes in mouse genomic DNA without the need for empiric optimization or synthesis of new probe variants.

The Leptin primers and probes were synthesized (Integrated DNA Technologies, Coralville, Iowa). The "T" probe was labeled with FAM (6-carboxyfluorescein) and the "C" probe was labeled with HEX (hexachlorofluorescein); both probes employed the Iowa Black FQ (IBFQ) quencher. Quantitative real-time PCR was performed using 2 ng genomic DNA per 10 μL reaction with Immolase™ DNA Polymerase (Bioline, Randolph, Mass.), 400 nM of each primer, and 200 nM of each probe. Reactions were run on a BIO-RAD® CFX384 Real-Time PCR Detection System (BIO-RAD, Hercules, Calif.). Cycling conditions employed were: 95° C. for 10 minutes followed by 45 cycles of 2-step PCR with 95° C. for 15 seconds and 60° C. for 1 minute. All reactions were performed in triplicate. Expression data were normalized. Genomic DNAs from 9 mice of known genotype at this SNP site in the Leptin gene were obtained from Jackson Labs (Bar Harbor, Me.) and included three homozygous C/C, three homozygous T/T, and three heterozygous C/T samples. Results are shown in FIGS. 2-5.

FIG. 2 shows an amplification plot using DNA from a homozygous C/C animal. Fluorescence signal was detected

TABLE 7

| Name | Sequence | Predicted $T_m$ Match | Predicted $T_m$ Mismatch | Predicted $\Delta T_m$ |
|---|---|---|---|---|
| For primer | CAGTCTATCAACAGGTCCTCAC | 63.7° C. | — | — |
| Rev primer | GGAGCAGCTCTTGGAGAAGG | 66.8° C. | — | — |
| Lep "C" probe | HEX-AGAATCT + C + C + GAGACCT-IBFQ | 66.5° C. | 54.5° C. | 12.0° C. |
| Lep "T" probe | FAM-AGAATCT + C + T + GAGACCTC-IBFQ | 63.3° C. | 57.4° C. | 5.9° C. |

Figure 3:
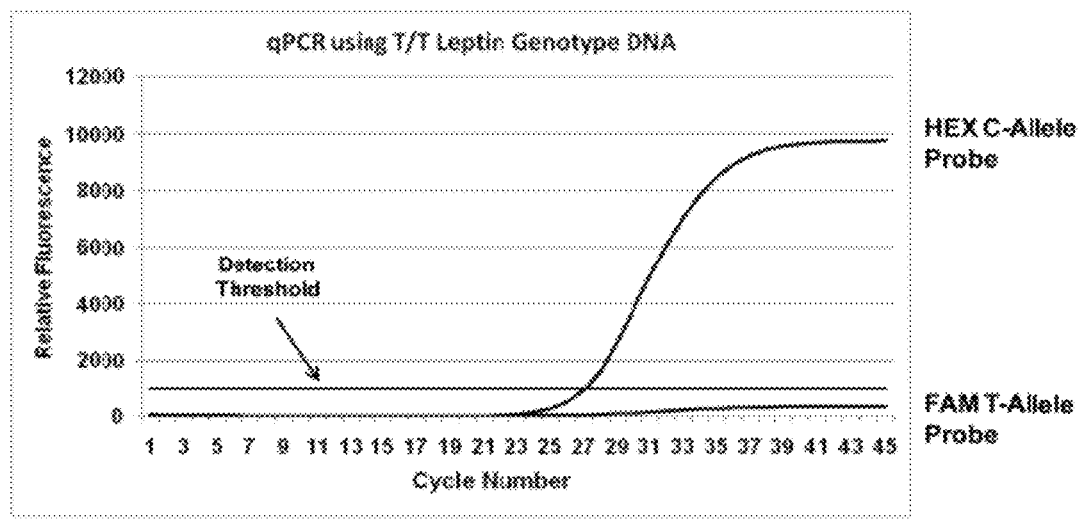
FIG. 3 shows an amplification plot of a real-time PCR reaction performed using genomic DNA homozygous for the T leptin locus (T/T genotype). Cycle number is shown on the X-axis and relative fluorescence is shown on the Y-axis. The FAM labeled T-specific probe showed positive signal whereas the HEX labeled C-specific probe remained undetectable at background levels.
Figure 4:
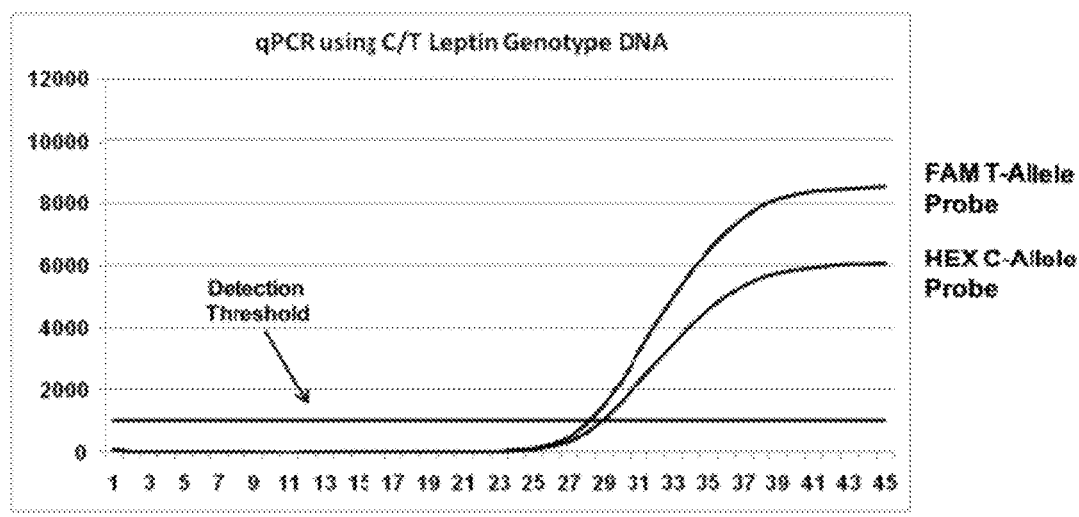
FIG. 4 shows an amplification plot of a real-time PCR reaction performed using genomic DNA heterozygous at this site in the leptin gene (C/T genotype). Cycle number is shown on the X-axis and relative fluorescence is shown on the Y-axis. Both the FAM labeled T-specific probe showed and the HEX labeled C-specific probe showed positive signal.
Figure 5:
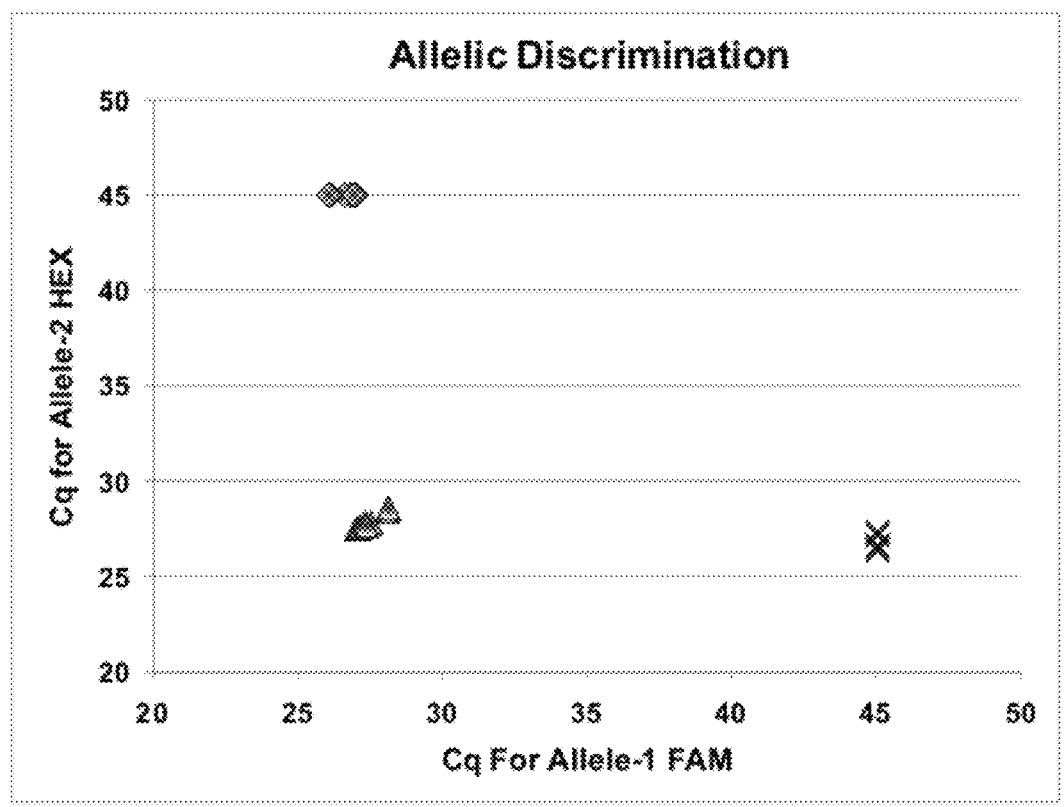
FIG. 5 is a plot showing the Cq value (cycle number where signal was first detected) for the FAM channel ("T" allele probe) on the X-axis and for the HEX channel ("C" allele probe) on the Y-axis. Values obtained from qPCR reactions performed on 9 mouse genomic DNA samples were used, including 3 homozygous C/C ("X"), 3 homozygous T/T ("◇"), and 3 heterozygous C/T ("Δ") animals. Reactions were performed in triplicate, therefore 27 data points are clustered in the plot.

DNA bases are uppercase; LNA bases are indicated as "+N"

in the HEX channel ("C" probe) at 27 cycles but no signal was detected in the FAM channel ("T" probe). FIG. 3 shows an amplification plot using DNA from a homozygous T/T animal. Fluorescence signal was detected in the FAM channel ("T" probe) at 27 cycles but no signal was detected in the HEX channel ("C" probe). FIG. 4 shows an amplification plot using DNA from a heterozygous C/T animal. Fluorescence signal was detected in both the FAM and the HEX channels at 27 and 28 cycles, respectively. Therefore, the probes correctly identified animals having C/C genotype, T/T genotype, and C/T genotype with no incorrect cross reactivity. FIG. 5 shows a summary plot of the Cq values (cycle number at which signal first was detected) for all 9 animals studied (3 PCR reactions done on 9 DNA samples=27 data points in total). The genotype of all 9 animals was correctly identified by the Leptin assay designed using the method of the present invention.

It is important to note that these assays worked using the first designs produced using the method of the present invention and no undesired cross-reactivity was observed. It was not necessary to test additional design variations as the first designs produced by the method worked as desired.

EXAMPLE 4

Also analyzed were Tm predictions for 11 duplexes from published sources where one strand was LNA modified from 89 to 100%. The calculations used herein assume that initiation parameters for terminal LNAs are identical to DNA initiation parameters (Santa Lucia, 1998) and predicted melting temperatures were corrected from 1M Na$^+$ to lower salt concentrations using equation 22 from Owczarzy et al., 2004. Table 8 presents predictions of matched LNA·DNA duplexes where one strand is completely or almost completely LNA-modified. The average error of Tm predictions was higher for these duplexes (2.7° C.) than the error observed for the set of VAL-01 to VAL-33 duplexes (1.5° C.). If an LNA strand is modified 40% or more, LNAs induce structural changes that could propagate beyond neighboring base pairs. In that case, the nearest-neighbor model may break down and reported LNA parameters would be less accurate.

TABLE 8

| Reference[b] | Sequence (5' to 3') | $C_t$ [μM] | Na$^+$ [M] | Experimental $T_m$ [° C.] | Predicted $T_m$ [° C.] | $T_m$ prediction error [° C.] |
|---|---|---|---|---|---|---|
| 1 | +C + C + T + C + G + C + C + T | 3 | 0.3 | 80.0 | 80.9 | 0.9 |
| 1 | +C + C + T + T + G + C + C + T | 3 | 0.3 | 71.0 | 76.7 | 5.7 |
| 1 | +A + G + G + C + A + A + G + G | 3 | 0.3 | 77.0 | 77.5 | 0.5 |
| 2 | +C + A + C + A + C + T + C + A + A + T + A | 3 | 0.115 | 69.0 | 68.3 | -0.7 |
| 3 | +G + G + C + G + C + T + T + CT | 2 | 0.115 | 75.6 | 73.5 | -2.1 |
| 3 | +G + G + C + A + C + T + T + CT | 2 | 0.115 | 66.9 | 68.7 | 1.8 |
| 3 | +C + G + C + G + C + A + C + GT | 2 | 0.115 | 68.5 | 76.8 | 8.3 |
| 3 | +C + G + C + A + C + A + C + GT | 2 | 0.115 | 70.6 | 72.3 | 1.7 |
| 3 | +C + C + G + C + G + C + A + CT | 2 | 0.115 | 72.7 | 79.7 | 7.0 |
| 3 | +G + C + C + G + C + G + C + AC | 2 | 0.115 | 79.0 | 80.4 | 1.4 |
| 4 | +G + T + G + A + T + A + T + G + C | 3 | 0.115 | 64.0 | 64.0 | 0.0 |

[b]References:
1. Ørum et al., 1999, *Clin. Chem.* 45: 1898-905.
2. Sørensen et al., 2002, *J. Am. Chem. Soc.* 124: 2164-76.
3. Jacobsen et al., 2002, *Nucleic Acids Res.* 30: e100.
4. Ørum and Wengel, 2001, *Curr. Opin. Mol. Ther.* 3: 239-43.

SEQUENCE LISTING

<160> NUMBER OF SEQ ID NOS: 97

<210> SEQ ID NO 1
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature

```
<222> LOCATION: (5)..(5)
<223> OTHER INFORMATION: Locked nucleic acid

<400> SEQUENCE: 1 ccgaagcc                                                                    8

<210> SEQ ID NO 2
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 2 ccgacgcc                                                                    8

<210> SEQ ID NO 3
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 3 ccgaggcc                                                                    8

<210> SEQ ID NO 4
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 4 ccgatgcc                                                                    8

<210> SEQ ID NO 5
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
```

```
<221> NAME/KEY: misc_feature
<222> LOCATION: (5)..(5)
<223> OTHER INFORMATION: Locked nucleic acid

<400> SEQUENCE: 5 ccgcagcc                                                                8

<210> SEQ ID NO 6
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 6 cagccgtc                                                                8

<210> SEQ ID NO 7
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 7 ctgcggac                                                                8

<210> SEQ ID NO 8
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 8 ccgctgcc                                                                8

<210> SEQ ID NO 9
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
```

```
<220> FEATURE:
<221> NAME/KEY: misc_feature
<222> LOCATION: (5)..(5)
<223> OTHER INFORMATION: Locked nucleic acid

<400> SEQUENCE: 9 ccggagcc                                                                  8

<210> SEQ ID NO 10
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 10 ctggcgac                                                                  8

<210> SEQ ID NO 11
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 11 ccggtgcc                                                                  8

<210> SEQ ID NO 12
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 12 ccgtagcc                                                                  8

<210> SEQ ID NO 13
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
```

```
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 13 ccgtcgcc                                                                       8

<210> SEQ ID NO 14
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 14 ccgtggcc                                                                       8

<210> SEQ ID NO 15
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 15 ccgttgcc                                                                       8

<210> SEQ ID NO 16
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 16 ggaaacgc                                                                       8

<210> SEQ ID NO 17
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 17 ggaaccgc                                                                 8

<210> SEQ ID NO 18
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 18 ggaagcgc                                                                 8

<210> SEQ ID NO 19
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 19 ggaatcgc                                                                 8

<210> SEQ ID NO 20
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 20 ggacacgc                                                                 8

<210> SEQ ID NO 21
<211> LENGTH: 8
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 21 ggacccgc                                                                    8

<210> SEQ ID NO 22
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 22 ggacgcac                                                                    8

<210> SEQ ID NO 23
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 23 ggactcgc                                                                    8

<210> SEQ ID NO 24
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 24 ggagacgc                                                                    8

<210> SEQ ID NO 25
<211> LENGTH: 8
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 25 ggagccgc                                                                   8

<210> SEQ ID NO 26
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 26 cgtggtag                                                                   8

<210> SEQ ID NO 27
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 27 acaggagt                                                                   8

<210> SEQ ID NO 28
<211> LENGTH: 8
<212> TYPE: DNA
<213> ORGANISM: Artificial Sequence
<220> FEATURE:
<223> OTHER INFORMATION: Synthetic

<400> SEQUENCE: 28 ggagtcgc                                                                   8

<210> SEQ ID NO 29
<211> LENGTH: 8
<212> TYPE: DNA
<213> ORGANISM: Artificial Sequence
<220> FEATURE:
<223> OTHER INFORMATION: Synthetic

<400> SEQUENCE: 29 ggatacgc                                                                   8

<210> SEQ ID NO 30
```

-continued

```
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 30 gcatccgc                                                                   8

<210> SEQ ID NO 31
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 31 ggatgcgc                                                                   8

<210> SEQ ID NO 32
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid

<400> SEQUENCE: 32 ggattcgc                                                                   8

<210> SEQ ID NO 33
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid

<400> SEQUENCE: 33
atcttttcca                                                                10
```

```
<210> SEQ ID NO 34
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 34
atcaaaatta                                                          10

<210> SEQ ID NO 35
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 35
atctttttca                                                          10

<210> SEQ ID NO 36
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid
```

```
<400> SEQUENCE: 36
atcatattta                                                              10

<210> SEQ ID NO 37
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 37
atccgcgtta                                                              10

<210> SEQ ID NO 38
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 38
atccgcgtta                                                              10

<210> SEQ ID NO 39
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
```

```
<220> FEATURE:
<221> NAME/KEY: misc_feature
<222> LOCATION: (7)..(7)
<223> OTHER INFORMATION: Locked nucleic acid

<400> SEQUENCE: 39
tactctctta                                                              10

<210> SEQ ID NO 40
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 40
atcacactta                                                              10

<210> SEQ ID NO 41
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 41
atctgtgtta                                                              10

<210> SEQ ID NO 42
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
```

```
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 42
atccagctta                                                              10

<210> SEQ ID NO 43
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 43
atcgtaatat                                                              10

<210> SEQ ID NO 44
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 44
atctggctta                                                              10

<210> SEQ ID NO 45
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 45
atcccttaat                                                          10

<210> SEQ ID NO 46
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 46
tacatcatta                                                          10

<210> SEQ ID NO 47
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 47
atcttgttta                                                          10

<210> SEQ ID NO 48
<211> LENGTH: 10
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 48
atcgggttac                                                          10

<210> SEQ ID NO 49
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid

<400> SEQUENCE: 49
atcttttca                                                           10

<210> SEQ ID NO 50
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid
```

```
<400> SEQUENCE: 50
atcttttca                                                              10

<210> SEQ ID NO 51
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Locked nucleic acid
<220> FEATURE:
<221> NAME/KEY: misc_feature
<222> LOCATION: (3)..(3)
<223> OTHER INFORMATION: Locked nucleic acid
<220> FEATURE:
<221> NAME/KEY: misc_feature
<222> LOCATION: (7)..(7)
<223> OTHER INFORMATION: Locked nucleic acid
<220> FEATURE:
<221> NAME/KEY: misc_feature
<222> LOCATION: (8)..(8)
<223> OTHER INFORMATION: Locked nucleic acid

<400> SEQUENCE: 51
atcttttca                                                              10

<210> SEQ ID NO 52
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
<223> OTHER INFORMATION: Locked nucleic acid

<400> SEQUENCE: 52 ggaaccgc                                                               8

<210> SEQ ID NO 53
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Locked nucleic acid
<220> FEATURE:
<221> NAME/KEY: misc_feature
<222> LOCATION: (4)..(4)
<223> OTHER INFORMATION: Locked nucleic acid
<220> FEATURE:
<221> NAME/KEY: misc_feature
<222> LOCATION: (5)..(5)
<223> OTHER INFORMATION: Locked nucleic acid
<220> FEATURE:
<221> NAME/KEY: misc_feature
<222> LOCATION: (6)..(6)
```

<223> OTHER INFORMATION: Locked nucleic acid

<400> SEQUENCE: 53 ggaaccgc                                                                    8

<210> SEQ ID NO 54
<211> LENGTH: 17
<212> TYPE: DNA
<213> ORGANISM: Artificial Sequence
<220> FEATURE:
<223> OTHER INFORMATION: Synthetic

<400> SEQUENCE: 54
tgacggagcg attcagc                                                         17

<210> SEQ ID NO 55
<211> LENGTH: 17
<212> TYPE: DNA
<213> ORGANISM: Artificial Sequence
<220> FEATURE:
<223> OTHER INFORMATION: Synthetic

<400> SEQUENCE: 55
tgacggagcg attcagc                                                         17

<210> SEQ ID NO 56
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 56
tgacggagcg attcagc                                                         17

<210> SEQ ID NO 57
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 57
tgacggagcg attcagc                                                         17

<210> SEQ ID NO 58
<211> LENGTH: 17
<212> TYPE: DNA
<213> ORGANISM: Artificial Sequence
<220> FEATURE:
<223> OTHER INFORMATION: Synthetic

<400> SEQUENCE: 58
ctatccaggc attcgca                                                         17

<210> SEQ ID NO 59
<211> LENGTH: 17
<212> TYPE: DNA
<213> ORGANISM: Artificial Sequence

```
<220> FEATURE:
<223> OTHER INFORMATION: Synthetic

<400> SEQUENCE: 59
ctatccaggc attcgca                                                  17

<210> SEQ ID NO 60
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 60
ctatccaggc attcgca                                                  17

<210> SEQ ID NO 61
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 61
ctatccaggc attcgca                                                  17

<210> SEQ ID NO 62
<211> LENGTH: 17
<212> TYPE: DNA
<213> ORGANISM: Artificial Sequence
<220> FEATURE:
<223> OTHER INFORMATION: Synthetic

<400> SEQUENCE: 62
ttactgtcaa ggcaact                                                  17

<210> SEQ ID NO 63
<211> LENGTH: 17
<212> TYPE: DNA
<213> ORGANISM: Artificial Sequence
<220> FEATURE:
<223> OTHER INFORMATION: Synthetic

<400> SEQUENCE: 63
ttactgtcaa ggcaact                                                  17

<210> SEQ ID NO 64
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 64
ttactgtcaa ggcaact                                                  17
```

<210> SEQ ID NO 65
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 65
ttactgtcaa ggcaact                                                  17

<210> SEQ ID NO 66
<211> LENGTH: 17
<212> TYPE: DNA
<213> ORGANISM: Artificial Sequence
<220> FEATURE:
<223> OTHER INFORMATION: Synthetic

<400> SEQUENCE: 66
gcgtcaagcg acatcat                                                  17

<210> SEQ ID NO 67
<211> LENGTH: 17
<212> TYPE: DNA
<213> ORGANISM: Artificial Sequence
<220> FEATURE:
<223> OTHER INFORMATION: Synthetic

<400> SEQUENCE: 67
gcgtcaagcg acatcat                                                  17

<210> SEQ ID NO 68
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 68
gcgtcaagcg acatcat                                                  17

<210> SEQ ID NO 69
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 69
gcgtcaagcg acatcat                                                  17

<210> SEQ ID NO 70
<211> LENGTH: 17
<212> TYPE: DNA
<213> ORGANISM: Artificial Sequence
<220> FEATURE:
<223> OTHER INFORMATION: Synthetic

```
<400> SEQUENCE: 70
cgacttgtcc ataccta                                                   17

<210> SEQ ID NO 71
<211> LENGTH: 17
<212> TYPE: DNA
<213> ORGANISM: Artificial Sequence
<220> FEATURE:
<223> OTHER INFORMATION: Synthetic

<400> SEQUENCE: 71
cgacttgtcc ataccta                                                   17

<210> SEQ ID NO 72
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 72
cgacttgtcc ataccta                                                   17

<210> SEQ ID NO 73
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 73
cgacttgtcc ataccta                                                   17

<210> SEQ ID NO 74
<211> LENGTH: 17
<212> TYPE: DNA
<213> ORGANISM: Artificial Sequence
<220> FEATURE:
<223> OTHER INFORMATION: Synthetic

<400> SEQUENCE: 74
ccatgcgtag acaagtg                                                   17

<210> SEQ ID NO 75
<211> LENGTH: 17
<212> TYPE: DNA
<213> ORGANISM: Artificial Sequence
<220> FEATURE:
<223> OTHER INFORMATION: Synthetic

<400> SEQUENCE: 75
ccatgcgtag acaagtg                                                   17

<210> SEQ ID NO 76
<211> LENGTH: 17
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 76
ccatgcgtag acaagtg                                                    17

<210> SEQ ID NO 77
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 77
ccatgcgtag acaagtg                                                    17

<210> SEQ ID NO 78
<211> LENGTH: 17
<212> TYPE: DNA
<213> ORGANISM: Artificial Sequence
<220> FEATURE:
<223> OTHER INFORMATION: Synthetic

<400> SEQUENCE: 78
ctatcgcatc taataat                                                    17

<210> SEQ ID NO 79
<211> LENGTH: 17
<212> TYPE: DNA
<213> ORGANISM: Artificial Sequence
<220> FEATURE:
<223> OTHER INFORMATION: Synthetic

<400> SEQUENCE: 79
ctatcgcatc taataat                                                    17

<210> SEQ ID NO 80
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 80
ctatcgcatc taataat                                                    17

<210> SEQ ID NO 81
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(10)
<223> OTHER INFORMATION: Locked nucleic acid

<400> SEQUENCE: 81
```
ctatcgcatc taataat                                                          17

<210> SEQ ID NO 82
<211> LENGTH: 100
<212> TYPE: DNA
<213> ORGANISM: Mus musculus

<400> SEQUENCE: 82
caccagcctg ccttcccaaa atgtgctgca gatagccaat gacctggaga atctcygaga           60
cctcctccat ctgctggcct tctccaagag ctgctccctg                                100

<210> SEQ ID NO 83
<211> LENGTH: 22
<212> TYPE: DNA
<213> ORGANISM: Artificial Sequence
<220> FEATURE:
<223> OTHER INFORMATION: Synthetic

<400> SEQUENCE: 83
cagtctatca acaggtcctc ac                                                    22

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
ggagcagctc ttggagaagg                                                       20

<210> SEQ ID NO 85
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: HEX (hexachlorofluorescein)
<220> FEATURE:
<221> NAME/KEY: misc_feature
<222> LOCATION: (16)..(16)
<223> OTHER INFORMATION: Iowa Black FQ (IBFQ) quencher

<400> SEQUENCE: 85
agaatctccg agacct                                                           16

<210> SEQ ID NO 86
<211> LENGTH: 17
<212> TYPE: DNA
<213> ORGANISM: Artificial Sequence
<220> FEATURE:
<223> OTHER INFORMATION: Sythetic
<220> FEATURE:
<221> NAME/KEY: misc_feature
<222> LOCATION: (1)..(1)
<223> OTHER INFORMATION: FAM (6-carboxyfluorescein)
<220> FEATURE:
<221> NAME/KEY: misc_feature
<222> LOCATION: (17)..(17)
<223> OTHER INFORMATION: Iowa Black FQ (IBFQ) quencher

<400> SEQUENCE: 86
agaatctctg agacctc                                                          17

```
<210> SEQ ID NO 87
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 87 cctcgcct                                                                  8

<210> SEQ ID NO 88
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 88 ccttgcct                                                                  8

<210> SEQ ID NO 89
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 89 aggcaagg                                                                  8

<210> SEQ ID NO 90
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(11)
<223> OTHER INFORMATION: Locked nucleic acid

<400> SEQUENCE: 90
cacactcaat a                                                             11

<210> SEQ ID NO 91
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 91 ggcgcttct                                                                 9
```

```
<210> SEQ ID NO 92
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 92 ggcacttct                                                                    9

<210> SEQ ID NO 93
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 93 cgcgcacgt                                                                    9

<210> SEQ ID NO 94
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 94 cgcacacgt                                                                    9

<210> SEQ ID NO 95
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 95 ccgcgcact                                                                    9

<210> SEQ ID NO 96
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: Locked nucleic acid

<400> SEQUENCE: 96
``` gccgcgcac 9

```
<210> SEQ ID NO 97
<211> LENGTH: 9
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Locked nucleic acid

<400> SEQUENCE: 97
``` gtgatatgc 9

What is claimed is:

1. A method of predicting the melting temperature of an oligonucleotide comprising:
   (a) a computer system receiving a data input from a user, the computer comprising a processor, and instructions executable by the processor;
   (b) responsive to the data input from a user, the computer system calculating a $T_m$ value using the equation:

$$T_m = \frac{\Delta H^o}{\Delta S^o + R\ln(C_1 - C_2/2)},$$

wherein $$\Delta H^\circ = \Delta H^\circ_{DNA} + \Delta\Delta H^\circ_{LNA}$$

and $$\Delta S^\circ = \Delta S^\circ_{DNA} + \Delta\Delta S^\circ_{LNA}; \text{ and}$$

(c) providing an output to a display;
   wherein the oligonucleotide comprises at least two Locked Nucleic Acid (LNA) modifications.

2. The method of claim 1, wherein $$\Delta\Delta H^o_{LNA} = \sum_{i,j=A,C,G,T} N_{ij}^{n-n} \Delta\Delta H_{ij}^{n-n}.$$

3. The method of claim 1, wherein $$\Delta\Delta S^o_{LNA} = \sum_{i,j=A,C,G,T} N_{ij}^{n-n} \Delta\Delta S_{ij}^{n-n}.$$

4. The method of claim 2 or 3, wherein the values are determined using nearest neighbor parameters.

5. A method of predicting the melting temperature of an oligonucleotide comprising:
   (a) a networked server receiving data input from a communication device associated with a user, the server comprising the communication interface, a processor, and instructions executable by the processor;
   (b) responsive to receiving the data input, the networked server sending via the communication interface to the communication device, calculation of a $T_m$ value using the equation:

$$T_m = \frac{\Delta H^o}{\Delta S^o + R\ln(C_1 - C_2/2)},$$

wherein $$\Delta H^\circ = \Delta H^\circ_{DNA} + \Delta\Delta H^\circ_{LNA}$$

and $$\Delta S^\circ = \Delta S^\circ_{DNA} + \Delta\Delta S^\circ_{LNA}; \text{ and}$$

(c) sending the $T_m$ value via the communication interface to the user communication device;
   wherein the oligonucleotide comprises at least two Locked Nucleic Acid (LNA) modifications.

6. The method of claim 5, wherein the user interacts with the networked server via a web-browsing application running on the communication device.

7. The method of claim 5, wherein the communication device comprises at least one of a computer, a desktop computer, or a laptop computer.

8. The method of claim 5, wherein $$\Delta\Delta H^o_{LNA} = \sum_{i,j=A,C,G,T} N_{ij}^{n-n} \Delta\Delta H_{ij}^{n-n}.$$

9. The method of claim 5, wherein $$\Delta\Delta S^o_{LNA} = \sum_{i,j=A,C,G,T} N_{ij}^{n-n} \Delta\Delta S_{ij}^{n-n}.$$

10. The method of claim 8 or 9, wherein the values are determined using nearest neighbor parameters.

* * * * *